(12) United States Patent
Kass et al.

(10) Patent No.: US 7,894,849 B2
(45) Date of Patent: Feb. 22, 2011

(54) MOBILE PERSONAL SERVICES PLATFORM FOR PROVIDING FEEDBACK

(75) Inventors: Alex M. Kass, Palo Alto, CA (US); Lucian P. Hughes, Half Moon Bay, CA (US); Owen E. Richter, Santa Clara, CA (US); Dana Le, San Francisco, CA (US); Daniel Farina, Belmont, CA (US)

(73) Assignee: Accenture Global Services Limited, Dublin (IE)

( * ) Notice: Subject to any disclaimer, the term of this patent is extended or adjusted under 35 U.S.C. 154(b) by 441 days.

(21) Appl. No.: 11/775,026

(22) Filed: Jul. 9, 2007

(65) Prior Publication Data

US 2008/0012701 A1    Jan. 17, 2008

Related U.S. Application Data

(60) Provisional application No. 60/830,127, filed on Jul. 10, 2006.

(51) Int. Cl.
| | |
|---|---|
| H04M 1/00 | (2006.01) |
| H04M 3/42 | (2006.01) |
| H04M 3/00 | (2006.01) |
| H04M 11/04 | (2006.01) |
| H04B 1/38 | (2006.01) |
| H04H 40/00 | (2008.01) |
| H04W 4/00 | (2009.01) |
| H04W 24/00 | (2009.01) |
| G10L 15/00 | (2006.01) |
| G10L 15/04 | (2006.01) |
| G10L 11/00 | (2006.01) |

(52) U.S. Cl. .................. 455/550.1; 455/414.1; 455/566; 455/420; 455/3.06; 455/466; 455/456.1; 455/404.1; 340/539.11; 340/521; 340/573.1; 340/574; 704/236; 704/251; 704/270

(58) Field of Classification Search .............. 455/550.1, 455/414.1, 566, 420, 3.06, 466, 456.1, 404.1; 340/539.11, 521, 573.1, 574; 704/236, 251, 704/270
See application file for complete search history.

(56) References Cited

U.S. PATENT DOCUMENTS 7,283,962 B2 * 10/2007 Meyerhoff et al. .......... 704/270

(Continued)

FOREIGN PATENT DOCUMENTS

EP    1089246 A2    4/2001

(Continued)

OTHER PUBLICATIONS

International Search Report dated May 15, 2008 in Int'l App. No. PCT/US2007/03058.

(Continued)

*Primary Examiner*—Matthew D. Anderson
*Assistant Examiner*—Bobbak Safaipour
(74) *Attorney, Agent, or Firm*—Fish & Richardson P.C.

(57) ABSTRACT

Methods, systems, and apparatus, including computer program products, for generating feedback. In one aspect, a method includes receiving sensor data from a plurality of sensors, wherein at least one of the plurality of sensors is associated with a mobile device of a user; aggregating the received sensor data to generate aggregated sensor data; processing the aggregated sensor data to determine an aggregated metric; comparing the aggregated metric to a target associated with the user to determine a measure of performance; and generating feedback based on the determined measure of performance. Further, the mobile device can comprise a mobile personal services device that includes one or more of an audio sensor, a video sensor, an environmental sensor, a biometric sensor, a location sensor, an activity detector, and a health monitor. The feedback can be displayed on the mobile personal services device. The feedback also can be displayed in near real-time.

18 Claims, 14 Drawing Sheets

U.S. PATENT DOCUMENTS

| | | | |
|---|---|---|---|
| 7,398,213 B1* | 7/2008 | Levanon et al. | 704/271 |
| 7,558,622 B2* | 7/2009 | Tran | 600/509 |
| 2003/0033145 A1* | 2/2003 | Petrushin | 704/236 |
| 2003/0078768 A1* | 4/2003 | Silverman et al. | 704/206 |
| 2004/0122487 A1* | 6/2004 | Hatlestad et al. | 607/60 |
| 2006/0178159 A1* | 8/2006 | Timms et al. | 455/518 |
| 2007/0103317 A1* | 5/2007 | Zellner et al. | 340/573.1 |
| 2007/0173266 A1* | 7/2007 | Barnes, Jr. | 455/456.1 |
| 2008/0009300 A1* | 1/2008 | Vuong | 455/466 |
| 2008/0064326 A1* | 3/2008 | Foster et al. | 455/3.06 |
| 2008/0132220 A1* | 6/2008 | Fitzgibbon | 455/420 |
| 2008/0133230 A1* | 6/2008 | Herforth | 704/235 |
| 2008/0243005 A1* | 10/2008 | Jung et al. | 600/481 |
| 2009/0288131 A1* | 11/2009 | Kandekar et al. | 725/133 |
| 2010/0063880 A1* | 3/2010 | Atsmon et al. | 705/14.53 |

FOREIGN PATENT DOCUMENTS

| | | |
|---|---|---|
| GB | 2345183 A | 6/2000 |
| WO | WO 02/078538 | 10/2002 |
| WO | WO 03/081578 A1 * | 2/2003 |
| WO | WO2005124722 A2 | 12/2005 |

OTHER PUBLICATIONS

Thomas Martin et al., "Issues in Wearable Computing For Medical Monitoring Applications: A case Study Of A Wearable ECG Monitoring Device" Wearable Computers, The Fourth International Symposium in Atlanta, GA, Oct. 16-17, 2000.

European Office Action for Application No. 07812726.3-1265 dated Oct. 27, 2010 (4 pages).

* cited by examiner

FIG. 9E

MOBILE PERSONAL SERVICES PLATFORM FOR PROVIDING FEEDBACK

This application claims the benefit of U.S. Provisional Application No. 60/830,127, filed Jul. 10, 2006. The disclosure of the prior application is considered part of (and is incorporated by reference in) the disclosure of this application.

TECHNICAL FIELD

The present disclosure relates to a mobile personal services platform, for example, a system that performs data collection regarding the activities of a user, and an application that performs analysis and provides feedback based on collected data.

BACKGROUND

A wide range of mobile personal devices are available to consumers for use in communicating with others, accessing information, collecting data, and organizing a multitude of tasks. For example, cell phones, electronic organizers, personal computers, MP3 players, and digital cameras all have achieved a significant level of market uptake. Further, some multi-function products have been introduced that combine two or more of these devices into a single unit. For example, smart phones can be configured to provide voice communication in conjunction with personal computer functionality that supports access to one or more data sources, including e-mail and network resources.

Additionally, specific purpose devices or sensors also are available for collecting data associated with a user, including health, location, activity, and fitness/wellness data. Data can be collected by a special purpose sensor worn or otherwise attached to a user. For example, glucose monitors collect data associated with blood sugar and pedometers collect data relating to activity. Further, portable heart monitors can be used to detect and record heart rate over a period of time, such that the results can be analyzed for trends and performance over time.

The data collected by a specific purpose sensor can be provided to a specialized application for analysis and feedback, such as a dedicated application hosted on a personal computer. Typically, the device housing the specific purpose sensor is coupled to a computer on which the specialized application is hosted and the collected data is transferred, e.g., via a wired data connection. The specialized application can then process the collected data to produce results and feedback in a form that is intelligible to the user. The specialized application generally is configured to process data corresponding to a single specific purpose sensor that relates to a single subject or system, such as glucose levels or heart rate.

SUMMARY

The present disclosure provides a method, a computer program product, and a system for collecting and analyzing sensor data associated with a device user, and for providing feedback based on the collected sensor data to the device user with respect to one or more habits.

The present inventors recognized a need to develop a system capable of using the omnipresence of a mobile device, such as a smart phone or personal digital assistant (PDA), on a user's body to assist the user in monitoring, managing, and enhancing one or more behaviors, improving communication, and/or accessing information. The inventors further recognized that such a system can be used for a wide variety of implementations, including habits management, memory enhancement, self-awareness enhancement, enhanced awareness of and interaction with the physical environment, and communications management. Additionally, the inventors recognized the need to provide near real-time feedback and time-delayed feedback to a user.

In general, in one aspect, the subject matter can be implemented to include receiving sensor data from a plurality of sensors, wherein at least one of the plurality of sensors is associated with a mobile device of a user; aggregating the received sensor data to generate aggregated sensor data; processing the aggregated sensor data to determine an aggregated metric; comparing the aggregated metric to a target associated with the user to determine a measure of performance; and generating feedback to the user based on the determined measure of performance. Further, the subject matter can be implemented such that the mobile device comprises a mobile personal services device that includes one or more of an audio sensor, a video sensor, an environmental sensor, a biometric sensor, a location sensor, an activity detector, and a health monitor.

The subject matter also can be implemented to include displaying the feedback on the mobile personal services device. Further, the subject matter can be implemented to include displaying the feedback in near real-time. Additionally, the subject matter can be implemented to include receiving location data from a location-based device indicating a current position of the mobile personal services device; and processing the aggregated sensor data in accordance with the received location data.

The subject matter also can be implemented such that at least one of the plurality of sensors is associated with a mobile personal services device of another user. Further, the subject matter can be implemented such that the sensor data is received in real-time. Additionally, the subject matter can be implemented to include processing the received sensor data associated with at least one of the plurality of sensors to determine a second metric; computing a composite score based on the aggregated metric and the second metric; and generating feedback based on the composite score.

In general, in another aspect, the techniques can be implemented as a computer program product, encoded on a computer-readable medium, operable to cause data processing apparatus to perform operations including receiving sensor data from a plurality of sensors, wherein at least one of the plurality of sensors is associated with a mobile device of a user; aggregating the received sensor data to generate aggregated sensor data; processing the aggregated sensor data to determine an aggregated metric; comparing the aggregated metric to a target associated with the user to determine a measure of performance; and generating feedback to the user based on the determined measure of performance. Further, the subject matter can be implemented such that the mobile device comprises a mobile personal services device that includes one or more of an audio sensor, a video sensor, an environmental sensor, a biometric sensor, a location sensor, an activity detector, and a health monitor.

The subject matter also can be implemented such that the computer program product is further operable to cause data processing apparatus to perform operations comprising displaying the feedback on the mobile personal services device. Additionally, the subject matter can be implemented such that the computer program product is further operable to cause data processing apparatus to perform operations comprising displaying the feedback in near real-time. Further, the subject matter can be implemented such that the sensor data is received in real-time.

The subject matter also can be implemented such that the computer program product is further operable to cause data processing apparatus to perform operations comprising receiving location data from a location-based device indicating a current position of the mobile personal services device; and processing the aggregated sensor data in accordance with the received location data. Further, the subject matter can be implemented such that at least one of the plurality of sensors is associated with a mobile personal services device of another user. Additionally, the subject matter can be implemented such that the computer program product is further operable to cause data processing apparatus to perform operations comprising processing the received sensor data associated with at least one of the plurality of sensors to determine a second metric; computing a composite score based on the aggregated metric and the second metric; and generating feedback based on the composite score.

In general, in another aspect, the subject matter can be implemented as a system including a plurality of mobile devices, wherein each mobile device includes at least one sensor; and a coach server configured to perform operations comprising receiving sensor data from a plurality of sensors, wherein at least one of the plurality of sensors is associated with a mobile device of a user; aggregating the received sensor data to generate aggregated sensor data; processing the aggregated sensor data to determine an aggregated metric; comparing the aggregated metric to a target associated with the user to determine a measure of performance; and generating feedback to the user based on the determined measure of performance. Further, the subject matter can be implemented such that the mobile device comprises a mobile personal services device that includes one or more of an audio sensor, a video sensor, an environmental sensor, a biometric sensor, a location sensor, an activity detector, and a health monitor.

The subject matter also can be implemented such that the mobile personal services device of the user further comprises a display configured to present the generated feedback. Further, the subject matter can be implemented such that the coach server is further configured to perform operations comprising transmitting the generated feedback to the mobile personal services device of the user in near real-time. Additionally, the subject matter can be implemented such that the sensor data is received in real-time.

The subject matter also can be implemented to include a location-based device that transmits location data. Further, the subject matter can be implemented such that the coach server is further configured to perform operations comprising receiving location data indicating a current location of the mobile personal services device of the user; and processing the aggregated sensor data in accordance with the received location data. Additionally, the subject matter can be implemented such that at least one of the plurality of sensors is associated with a mobile personal services device of another user. The subject matter further can be implemented such that the coach server is further configured to perform operations comprising processing the received sensor data associated with at least one of the plurality of sensors to determine a second metric; computing a composite score based on the aggregated metric and the second metric; and generating feedback based on the composite score.

The techniques described in this specification can be implemented to realize one or more of the following advantages. For example, the techniques can be implemented such that a user's progress toward one or more goals can be measured and quantified. The techniques also can be implemented such that sensor data is collected, formatted, and transmitted in a standardized manner by devices included in the mobile personal services platform. Further, the techniques can be implemented such that near real-time feedback associated with one or more habits can be provided to a user. Additionally, the techniques can be implemented to permit providing one or more services to a user based on one or more detected parameters, including time and location data collected from a mobile personal services device worn by the user.

These general and specific techniques can be implemented using an apparatus, a method, a system, or any combination of an apparatus, methods, and systems. The details of one or more implementations are set forth in the accompanying drawings and the description below. Further features, aspects, and advantages will become apparent from the description, the drawings, and the claims.

BRIEF DESCRIPTION OF THE DRAWINGS

FIGS. 9A-9E show a habits coach interface.

DETAILED DESCRIPTION

Figure 1:
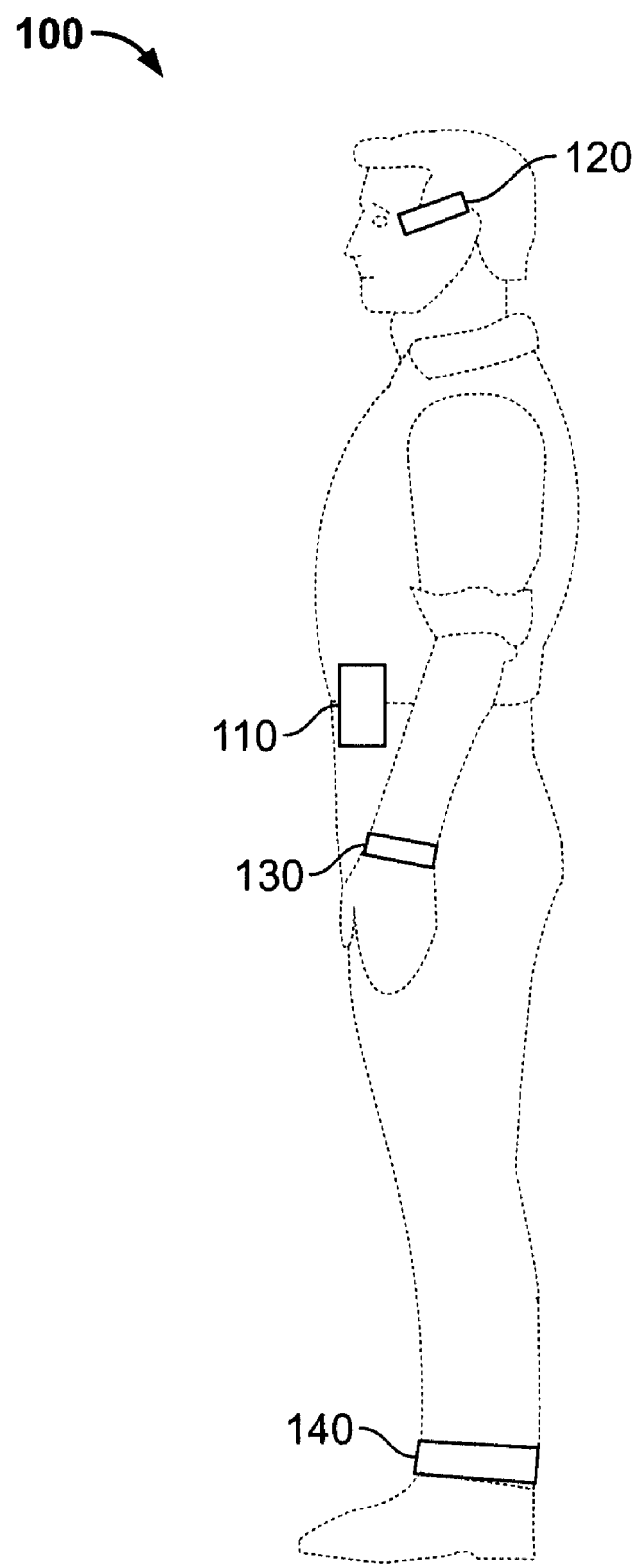
FIG. 1 shows a mobile personal services device.

FIG. 1 shows a mobile personal services device 100 that is wearable by a human user. The mobile personal services device 100 includes a personal device 110, such as a smart phone or a personal digital assistant (PDA), and a data sensing unit 120, such as a headpiece. The personal device 110 can be configured to receive input from a user through one or more of a keyboard, a touch pad, a stylus, a touch screen, a control wheel, a button, a microphone, and any other input interface known in the art. The personal device 110 also can be configured to provide output to a user through one or more of a screen, a heads up display, one or more speakers, headphones, haptic feedback, and any other output interface known in the art. Additionally, the mobile personal services device 100 can include a wireless network connection to permit the transfer of data to and from a network, such as the Internet, and the transfer of data to and from one or more mobile personal services device servers, such as a coach server 230.

The data sensing unit 120 can be configured to capture data associated with a human user through one or more personal sensors, including audio data, video data, location data, images, personal biometric data, and environmental data, such as temperature and humidity. The personal sensors can include any portable sensor that has a wireless or wired interface to the personal device 110, including a microphone, a still camera, a video camera, a biometric sensor, an environmental sensor, and a location sensor, such as a GPS receiver or beacon. The one or more personal sensors can be integrated with the data sensing unit 120 or coupled to the data sensing unit 120 through one or more wired or wireless communication channels. The mobile personal services device 100 can be configured to capture sensor data in a general and consistent manner, such that sensor data capture and reporting can be performed consistently across a plurality of applications. For example, modules configured to capture, report, store, and/or analyze sensor data can be generated by different parties using standardized sensor data formats and rules.

In an implementation, the personal device 110 can be configured to operate with a plurality of data sensing units 120. Further, the data sensing unit 120 can include one or more user interfaces, such as input interfaces and output interfaces. Additionally, a single device included in the personal device 110 or the data sensing unit 120, such as a microphone, can be configured to function as both a sensor and a user interface. The personal device 110 and the data sensing unit 120 also can be configured to communicate through a wired or wireless communication path.

The mobile personal services device 100 further can be configured to include additional sensor devices, such as a health monitor 130 and an activity detector 140. For example, the health monitor 130 can be configured to collect data regarding one or more physical measures, such as heart rate, blood pressure, glucose levels, temperature, etc. In another implementation, one or more of the devices included in the mobile personal services device 100 can be consolidated within a common housing. For example, the personal device 110 can be combined with the data sensing unit 120 to form a single device. Further, any additional devices, including any of the one or more health monitors 130 and the activity detector 140, can be consolidated into a single device or integrated into either of the personal device 110 and the data sensing unit 120.

Figure 2:
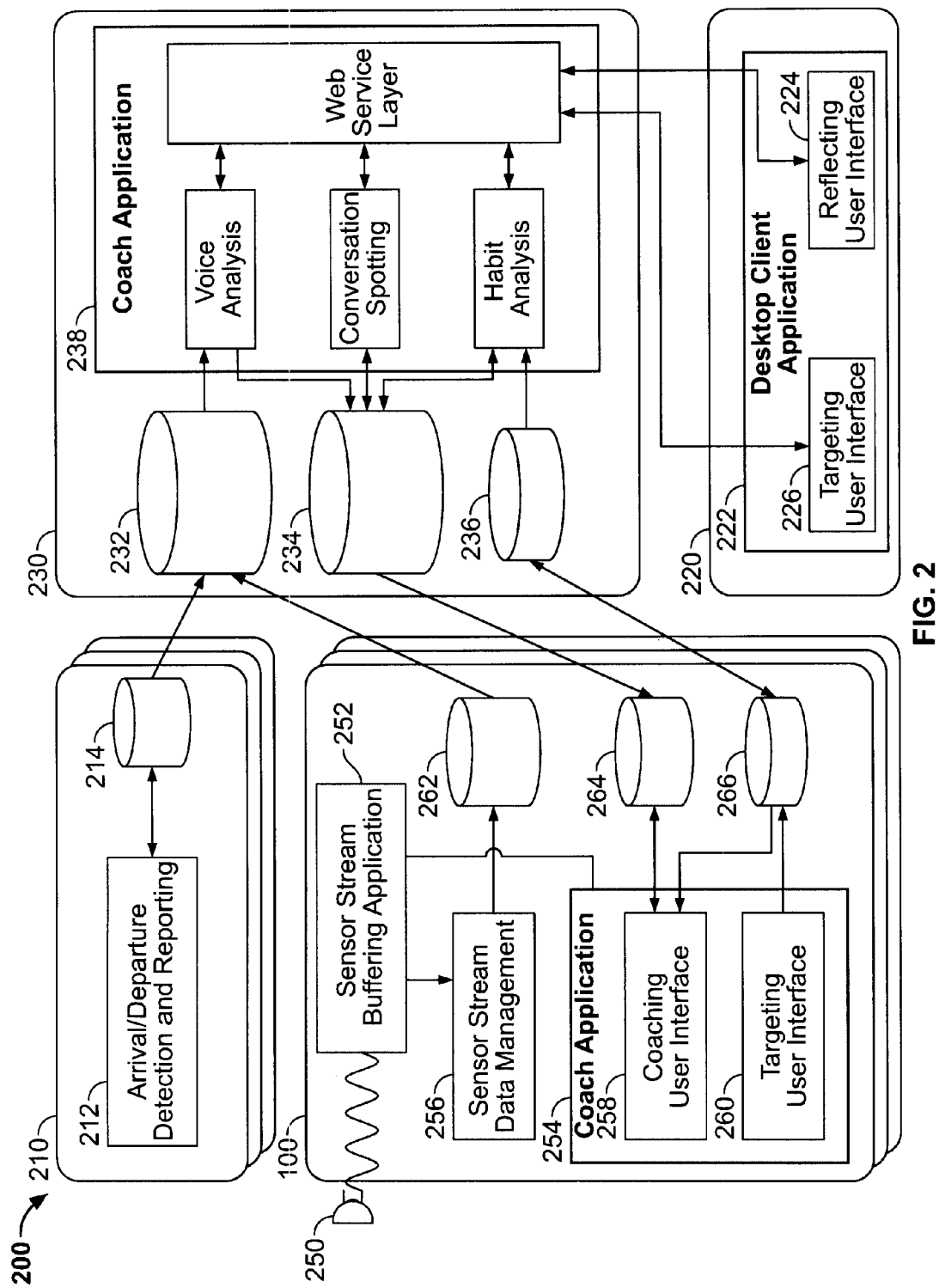
FIG. 2 is a diagram of a system architecture in which a coaching system can be configured to operate.

FIG. 2 presents a coaching system 200, also referred to as a mobile personal services platform, in which one or more mobile personal services devices 100 can be configured to operate. The coaching system 200 includes at least one mobile personal services device 100 and a coach server 230, and also can be configured to include one or more of a location-based device 210 and a coach client 220. The mobile personal services device 100, the location-based device 210, and the coach client 220 each can be configured to communicate directly with the coach server 230 through either a uni-directional communication path to the coach server 230 or a bi-directional communication path to and from the coach server 230.

One component of the mobile personal services device 100, such as the data sensing unit 120, can be configured to capture one or more sensor streams, including audio, video, and data. A personal sensor 250 can be included in the data sensing unit 120 for each type of sensor data that is to be captured. Further, a sensor stream buffering application 252 can receive sensor data from one or more personal sensors 250 and provide the sensor data to one or more additional applications hosted on the mobile personal services device 100. For example, the sensor stream buffering application 252 can provide sensor data to a coach application 254. Additionally, the coach application 254 can include one or more user interface modules, such as the coaching user interface 258 and the targeting user interface 260. The sensor stream buffering application 252 also can provide sensor data to a sensor stream data management module 256.

Within a mobile personal services device 100, data can be recorded in one or more datastores. For example, sensor stream data can be recorded in a local sensor stream datastore 262. The sensor stream data management module 256 can receive sensor data from the sensor stream buffering application 252 and record the sensor data in the sensor stream datastore 262 of the mobile personal services device 100. In another implementation, the sensor stream data management module 256 can be configured to communicate sensor data directly to a sensor stream datastore 232 associated with the coach server 230. The sensor stream data management module 256 can communicate the sensor data directly to the sensor stream datastore 232 at the coach server 230 as long as communication between the mobile personal services device 100 and the coach server 230 is possible. If communication between the mobile personal services device 100 and the coach server 230 is lost, the sensor stream buffering application 252 can record the sensor data in the sensor stream datastore 262 of the mobile personal services device 100. Further, when communication between the mobile personal services device 100 and the coach server 230 is restored, sensor data recorded in the sensor stream datastore 262 of the mobile personal services device 100 can be forwarded to the sensor stream datastore 232 at the coach server 230.

The sensor stream data also can be divided into a series of individual data units prior to storage or transmission. In the case of temporal sensor data, such as an audio or video stream, the sensor data can be partitioned into time slices, such that each slice represents a portion of a complete stream. For example, a slice can represent a duration of sensor stream data, such as 1 to 5 seconds. Further, information identifying one or more of the date and time the slice was recorded, one or more high resolution counter numbers, an identifier corresponding to the preceding slice, and one or more offsets, such as network time protocol offsets, also can be stored. Thus, one or more slices associated with a continuous stream of information that has an indeterminate length can be stored and accessed, even before the entire stream of information has been captured. Further, one or more slices corresponding to a stream of information between an arbitrary start and end time also can be accessed. For example, the slices that include information corresponding to the time range of interest can be retrieved. Further, any portion of a slice that falls outside of the time range of interest can be skipped or omitted.

A processed events datastore 264 can similarly be used to store data processed by one or more applications hosted on the personal device 110 and the coach server 230. Additionally, a targeting datastore 266 can be used to store targeting data associated with a user. Data captured by a mobile personal services device 100 or recorded in the datastores of a mobile personal services device 100 can be provided to one or more applications hosted on the personal device 110 and the coach server 230. In another implementation, the targeting user interface 260 can be configured to communicate directly with the targeting datastore 236 of the coach server. Further, targeting user interface 260 can store targeting data in the targeting datastore 266 of the mobile personal services device 100 when direct communication between the mobile personal services device 100 and the coach server 230 is not possible. Additionally, the targeting user interface 260 can be configured to communicate targeting data stored in the targeting datastore 266 to the targeting datastore 236 of the coach server once communication between the mobile personal services device 100 and the coach server 230 has been restored.

A location-based device 210 included in the coaching system 200 can be associated with a fixed location, such as a room, a passageway, or a non-mobile device. In an implementation, the location-based device 210 can be a Wi-Fi router. The location-based device 210 also can be configured to execute a detection and reporting application 212 to detect the presence of other devices included in the coaching system 200, such as mobile personal services devices 100. In an implementation, the location-based device 210 can detect the other device by sensing a Bluetooth beacon or Wi-Fi signal associated with that device.

In another implementation, a location-based device 210 can be configured to broadcast a signal that includes a location identifier corresponding to a particular location or device. The location identifier can be a unique identifier or can correspond to a plurality of locations or devices. Further, the location-based device 210 can broadcast the signal as a Bluetooth beacon or Wi-Fi signal. A mobile personal services device 100 can detect the signal from the location-based device 210 and transmit the location identifier to the coach server 230, such as in conjunction with one or more items of sensor data.

Additionally, a location-based device 210 associated with a particular location can be shielded, such that the signal broadcast by the location-based device 210 does not emanate beyond the location at a substantial level. Thus, the possibility of false reporting can be reduced. Alternatively, location detection can be performed based on detected Wi-Fi signal strength using any technique known in the art. For example, Wi-Fi signal strength can be used to perform proximity detection to determine which location-based device 210 or other such device is closest to the mobile personal services device 100. Thus, a location, such as a room, can be determined based on the signal received from one or more location-based devices 210.

In an implementation, the Wi-Fi signal strength associated with one or more location-based devices 210 can be captured by the mobile personal services device 100 and stored or transmitted to the coach server 230. The Wi-Fi signal strength data then can be analyzed to determine the mobile personal services device 100 location at a particular point in time. For example, the mobile personal services device 100 location can be determined to be proximal to the location-based device 210 broadcasting the strongest captured Wi-Fi signal strength. In another implementation, a plurality of signals can be compared to determine a more precise location, such as through triangulation. Further, Wi-Fi signal strength can be measured as an absolute or relative value. Additionally, analysis of Wi-Fi signal strength can be performed over a longer time period if accuracy is the primary concern or over a shorter time period if response time is the primary concern. Analysis can be performed continuously or in response to an analysis request. Also, analysis can be performed simultaneously with the receipt of data, such as in real-time or near real-time, and/or retroactively.

Further, the location-based device 210 can be relocated to identify a new fixed location. For example, the location-based device 210 can be a portable device that can be moved from a first room, such as an office, to a second room, such as a conference room. The location-based device 210 can then be associated with the new location, such as by reconfiguring location information included in the location-based device 210 or by updating information corresponding to the location-based device in the coach server 230. In another example, the location-based device 210 can be associated with a device, such as a photocopier or vending machine, that can be relocated. The location-based device 210 thus also can be used to track information associated with accessing the device, such as time, length, and/or frequency of access.

When the detection and reporting application 212 detects a mobile personal services device 100 entering or leaving the room, the location-based device 210 can transmit one or more reporting messages to the coach server 230. Further, the location-based device 210 also can be configured to include additional information in the one or more reporting messages, such as a time of detection, direction of movement (entry or exit), and a transaction conducted with a device with which the location-based device 210 is associated. Additionally, a location-based device 210 can include a datastore 214. The datastore 214 can be used to store information associated with the detection and reporting application, including data that is to be transmitted to the coach server 230.

In another implementation, instead of or in addition to transmitting reporting messages, a location-based device 210 can be configured to broadcast information, such as an identifier and a current time, to all devices within a fixed area. The location-based device 210 can be configured to broadcast information via infrared or radio-frequency, such as Bluetooth or Wi-Fi. The location-based device 210 further can be configured to broadcast a measure of Wi-Fi signal strength. Additionally, a location-based device 210 can be configured to broadcast synchronization information within a fixed area, such as one or more tones. The one or more tones can be in a frequency range that either is audible or inaudible to a human listener.

In an implementation, the one or more tones can be used to synchronize sensor data, such as sensor data comprising audio streams, captured by a plurality of sensors. In another implementation, a high resolution counter can be included in a mobile personal services device 100, such as in the personal device 110. The high resolution counter can be used to accurately measure relative times. Further, the personal device 110 can periodically query a time server, such as a Network Time Protocol (NTP) server, to determine the current time. To reduce any distortion caused by latency, the latency differences in receiving the time from the NTP server can be averaged over a plurality of requests to determine an average offset between the time reported by the NTP server and the count of the high resolution counter. The determined average offset, the count of the high resolution counter, and the time reported by the NTP server can be stored in the sensor stream data store 232 at the coach server 230 or the sensor stream data store 262 at the mobile personal services device 100 and can be used to synchronize sensor data associated with two or more mobile personal services devices. In an implementation, the sensor data associated with two or more mobile personal services devices can be synchronized with a resolution that provides a listener with the perception that the sensor data was recorded simultaneously, such as a resolution of 200 milliseconds or less.

The coach client 220 comprises a computing platform, such as a desktop, laptop, or work station. The coach client 220 can be configured to communicate with the coach server 230 over a wireless or wired communication path, including a private network, such as a local area network, and a public network, such as the Internet. In an implementation, the coach client 220 can be configured to communicate with the coach server 230 at the Web Service Layer.

Further, the coach client 220 can be configured to execute one or more application programs that receive data from, provide data to, or otherwise interact with the coach server 230. For example, the coach client 220 can execute a coaching client application 222 to provide feedback to a user based on collected data. Further, the coaching client application 222 can be configured to provide one or more user interfaces. For example, the coaching client application 222 can include a reflection user interface 224 to permit a user to receive feedback and a targeting user interface 226 to permit a user to specify goals or targets associated with one or more measures.

In an implementation, because the coach client 220 can be configured to include greater computing capability than a personal device 110, it is possible to configure an application hosted on the coach client 220, such as the coaching client application 222, to provide resource intensive features and functionality that are not available through a personal device 110.

The coach server 230 is configured to host one or more coaching applications and includes one or more datastores. The coach server 230 can be dedicated to a single user, such as a private server. Alternately, the coach server 230 can be associated with a plurality of users and can be managed by someone other than the mobile personal services device 100 user. For example, the coach server 230 can be managed by a service provider at a location remote from the user. Additionally, the coach server 230 can be configured to host applications that are proprietary to the service provider or a third-party content provider.

The coach server 230 can be implemented using a plurality of server platforms, such that the coach server 230 is scalable to the computing demands of the coaching system 200. Each of the one or more datastores included in the coach server 230 can be configured to store information relating to one or more specific functional areas. For example, a sensor stream datastore 232 can be used to store data transmitted to the coach server 230 by one or more location-based devices 210 and one or more mobile personal services devices 100. The sensor data can be stored such that a plurality of sensor streams can be cross-correlated. Further, the cross-correlated sensor data streams can correspond to any sensors. For example, sensor data corresponding to a user's health habits can be cross-correlated with sensor data corresponding to the user's conversation habits. Thus, the nature of the relationship between various user habits can be analyzed. Additionally, the coach server 230 also can be configured to analyze sensor data in conjunction with data from other sources, such as the Internet or expert systems. A processed events datastore 234 can similarly be used to store data processed by one or more applications hosted on the coach server. Additionally, a targets datastore 236 can be used to store target information associated with a user. In another implementation, the processed events datastore 234 of the coach server 230 and the processed events datastore 264 of the mobile personal services device 100 can be omitted, and the coaching user interface 258 can communicate directly with the web services layer of a coaching application 238.

A coaching application 238 hosted on the coach server 230 can be configured to manage and analyze high-volume sensor-stream data, such as data provided by a location-based device 210 and a mobile personal services device 100. In performing analysis, the coaching application 238 can be configured to aggregate two or more sensor-streams, such as two or more audio streams associated with a single conversation. Further, the two or more sensor-streams can be obtained from a plurality of separate mobile personal services devices. The coaching application 238 also can be configured to generate results relating to one or more metrics and to report the results to a device to provide feedback to a user, such as the personal device 110 or the coach client 220. Depending on the needs of a user at a particular point in time, the feedback can be provided in near real-time or time delayed. For example, near real-time feedback can be provided to the user through the personal device 110. This enables the user to review feedback soon after an event occurred. Time-delayed feedback can be presented to a user through a traditional computer, such as a laptop, desktop, or workstation. Thus, time-delayed feedback can be presented on a larger screen to allow for more detailed visualizations. The time-delayed feedback also can include more resource intensive functionality. In another implementation, both near real-time feedback and time-delayed feedback can be presented on a personal device 110 and a traditional computer.

Figure 3:
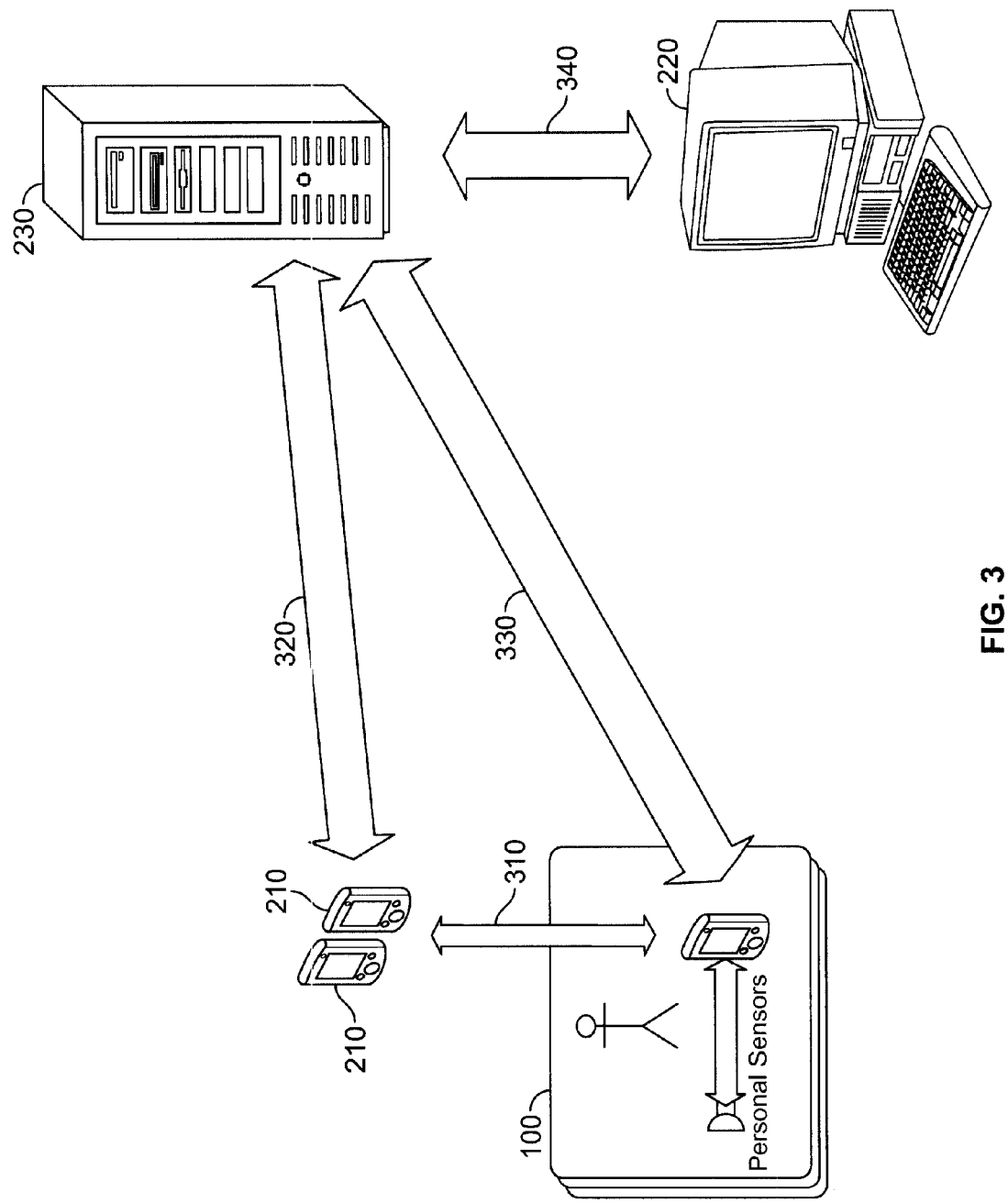
FIG. 3 shows communication channels between devices comprising a coaching system.

FIG. 3 depicts communications channels between the devices included in the coaching system 200. In an implementation, a location-based device 210 can communicate with a mobile personal services device 100 over a local communication path 310. The local communication path 310 can comprise any wireless communications technology, including radio frequency communications, such as Bluetooth or Wi-Fi, and infrared communications. A location-based device 210 can be configured to passively monitor a given location and to detect an identification signal, such as a Bluetooth beacon or Wi-Fi signal, broadcast by another device. Alternately, a location-based device 210 can be configured to periodically transmit information and to detect another device, such as a mobile personal services device 100, through a message exchange. For example, a location-based device 210 can be configured to broadcast the existence of a product or service, such as available inventory or special offers. The location-based device 210 can be configured to receive messages from other devices in response to the broadcast information and to record the identity of the responding device.

A location-based device 210 also can communicate with a coach server 230 via a location data path 320. The location data path 320 can comprise either a wireless or a wired communication path. Further, the location data path 230 can be bi-directional or uni-directional from the location-based device 210 to the coach server 230. For example, a location-based device 210 can be configured to communicate with a coach server 230 over a wireless connection using radio frequency transmissions, such as Wi-Fi or cellular signals. Alternately, a location-based device 210 can be configured to communicate with a coach server 230 over a wired connection, such as a computer network or telephone connection.

Further, a mobile personal services device 100 can communicate with a coach server 230 via a platform data path 330, which permits bi-directional communication between the mobile personal services device 100 and the coach server 230. The platform data path 330 can be configured as a wireless connection using radio frequency transmissions, such as Wi-Fi or cellular.

A coach client 220 can be configured to communicate with a coach server 230 via a client-server data path 340. The client-server data path 340 can comprise either a wireless or a wired communication path. For example, a coach client 220 can be configured to communicate with a coach server 230 over a wired connection, such as a computer network or telephone connection. Alternately, a coach client 220 can be configured to communicate with a coach server 230 over a wireless connection using radio frequency transmissions, such as Wi-Fi or cellular. In either instance, the coach client 220 can be configured to communicate with the coach server 230 at the Web Services Layer via the Transmission Control Protocol (TCP).

In an implementation of the mobile personal services device 100, a habits management coach can be used to monitor a user's habits, including conversation habits, health habits, and/or time management habits. For example, a conversation habits coach can be used to monitor a user's effectiveness during a conversation. For a specific conversation, the conversation habits coach can suggest one or more targets to a user. The targets can be established based on a number of factors, including the user's history, the type of conversation, the number of participants in the conversation, and the role of the user in the conversation, such as presenter, moderator, or client. Further, the user can adjust one or more targets to correspond to the user's personal targets for the conversation. For example, a conversation with a supervisor at work may have different targets than a conversation with a friend at a café. Additionally, the user may want to be especially respectful during a specific conversation and thus can choose to decrease the target associated with interruptions.

The conversation habits coach can be configured to analyze the conversation with respect to one or more selected targets and determine the user's performance with respect to those targets. For example, the targets can help gauge balance, such as identifying whether a user spent too much time talking or too much time listening. Additionally, the conversation habits coach can be configured to analyze the conversation with respect to content and procedure, including the number of questions asked, the number of times a user interrupted, changes in topic, inappropriate laughter, whether the user spoke too quickly or too slowly, changes in stress levels, changes in conversational tone, and the use of sarcasm. The conversation habits coach also can be configured to perform word-spotting or linguistic analysis, such as identifying the number of grammatical mistakes made or analyzing word choice. In another implementation, a human operator can analyze a conversation with respect to one or more topics, and can annotate specific occurrences using an application, such as the conversation habits coach.

In another implementation, the conversation habits coach can be configured to provide reminders, such as during a presentation or sales call. For example, a check list of specific points can be submitted to the conversation habits coach. Further, the conversation habits coach can be configured to monitor the user's speech, recognize that the user is making a specific point, check off the specific point after it has been made, and identify specific points that have not been made.

The conversation habits coach can be configured to monitor conversations throughout the day and to provide near real-time feedback during a conversation. Feedback is structured to help improve the user's conversation habits and to improve the user's effectiveness in communicating with others. The near real-time feedback can be provided to the user through any combination of audio, video, and text.

The conversation habits coach can collect data related to conversations throughout the day using one or more of the personal device 110, the data sensing unit 120, and the location-based devices 210. For example, the audio stream associated with a conversation can be captured by an audio sensor included in the data sensing unit 120. A conversation can be detected based on one or more events. For example, a conversation can be presumed when a user with an associated mobile personal services device 100 enters a room in which another user is present. Alternatively, a conversation can be presumed when two users are located within a certain range of one another and at least one of the users is speaking. Further, a conversation may not be presumed unless both users speak for a period of time that exceeds a threshold amount.

In an implementation, a conversation can be presumed based on one or more predetermined values associated with captured audio sensor data. An audio stream associated with an audio sensor, such as a microphone, can be converted into a stream of amplitude values. For example, integer values can be used to represent pressure associated with sound that oscillates in positive and negative values around a center value of zero. The square of the integer values can be computed to represent the amplitude values associated with an audio stream. Further, the average of the amplitude values over a predetermined period of time, such as 0.25 seconds, can be compared with a talkThreshold value that represents a minimum amplitude associated with speech. If the average amplitude exceeds the talkThreshold, speech can be presumed. Further, as described above, one or more additional items of data can be used to presume a conversation. For example, a conversation can be presumed based on the detection of speech in combination with the user's presence in a particular location and/or proximity to another person.

In an implementation, a nottalkingThreshold can be used to represent a maximum amplitude associated with not talking. If the average amplitude drops below the nottalkingThreshold, speech can be presumed to have ended. Further, a coughThreshold also can be used to filter out high amplitude events, such as a cough or physical contact with the microphone, that do not represent a talking event. Additionally, a timeDecay value can be established that reduces the talkThreshold and/or increases the nottalkingThreshold after the onset of talking so that short term pauses do not represent the end of a talking event.

The audio data comprising a conversation can be captured, divided into time slices, and buffered in a datastore located on the mobile personal services device 100. The mobile personal services device 100 can transmit the audio data to the coach server 230 at an appropriate data rate. Alternatively, audio data comprising a conversation can be transmitted directly to the coach server 230. A conversation also can be presumed to end based on one or more events. For example, a conversation can be presumed to have ended when one or more of the users exit the conversation, such as by leaving the physical location of the conversation. Alternatively, a conversation can be presumed to end only when all but one of the participants has exited the conversation. Further, a conversation may be presumed to end even when two or more participants remain in the same physical location if none of the participants has spoken for a threshold period of time. The audio streams associated with separate conversations in which the user participated can be separately identified. Separation facilitates the analysis of independent conversations. Further, separation also can be used to permit separate target setting and analysis.

Near real-time feedback can be provided to the user through the personal device 110. Depending on the latency due to communications and processing, near real-time feedback can be provided to a user as early as within seconds of when an event occurred. For some near real-time feedback, however, the feedback will not be provided to the mobile personal services device 100 for tens of minutes after an event occurred. For example, one or more metrics associated with the current conversation can be displayed to the user on a screen of the personal device 110, including information indicating the percentage of a conversation the user has spent speaking versus listening, as well as periods during which the participants of the conversation were silent.

Figure 4:
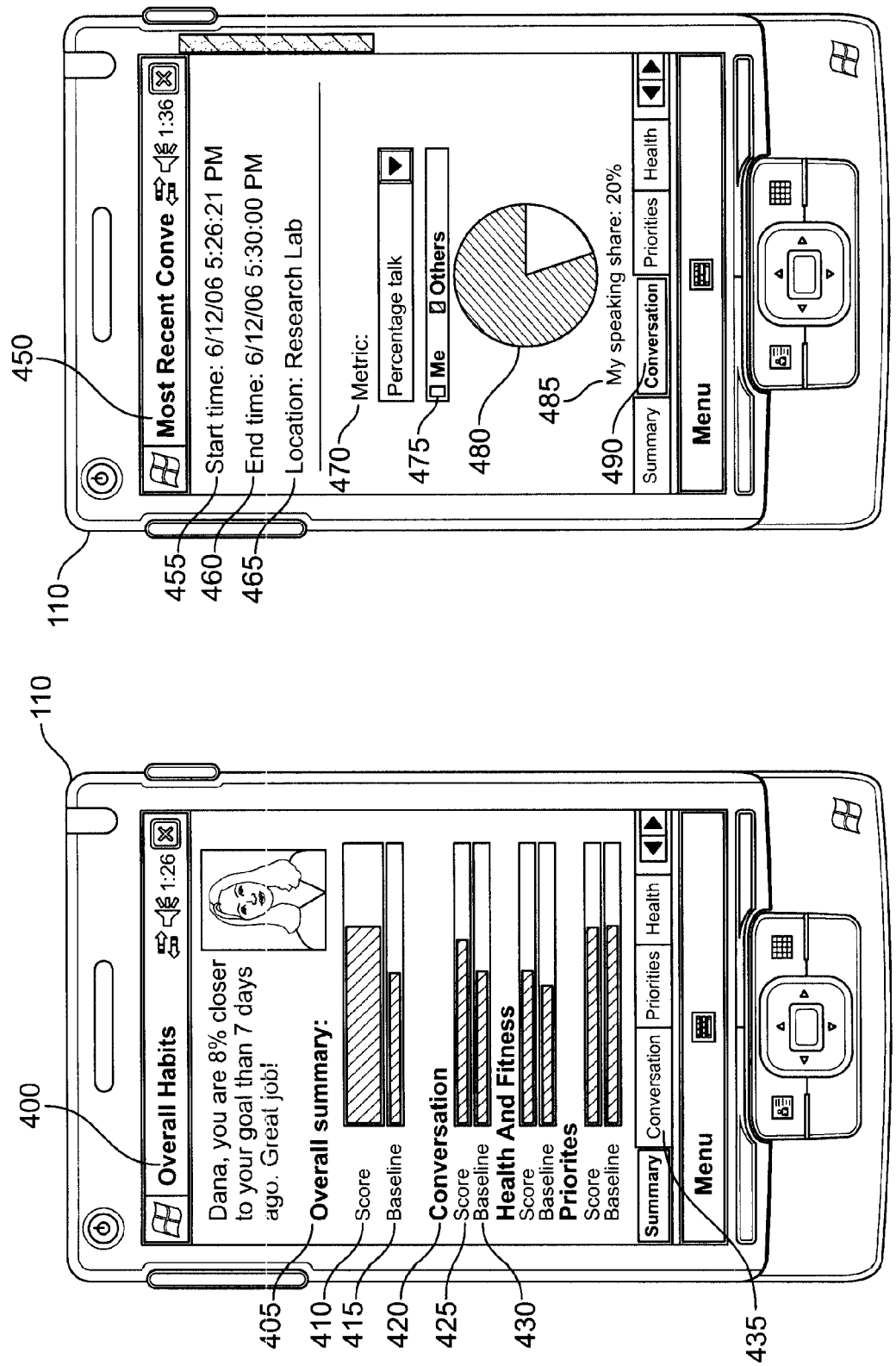
FIG. 4 shows feedback provided through a user interface on a personal device.

FIG. 4 depicts near real-time feedback presented on the personal device 110. The personal device 110 can include an overall habits interface 400, which can be configured to provide the user with access to information and applications relating to one or more coaching functions. The overall habits interface 400 can include an overall habits summary 405 that represents a user's progress at achieving goals associated with one or more habits, including conversation habits, health and fitness habits, and priorities habits. The overall habits summary 405 can include an overall score 410 that represents a user's current overall score for the habits that are being coached and an overall baseline 415.

The overall score 410 can be computed in a number of ways. In an implementation, a baseline, a goal, and a current score can be established for a habit. The baseline indicates the beginning point with respect to the habit and the current score indicates the user's current value for the habit. Further, the goal represents a target the user would like to achieve. For example, a user tracking their weight may have a goal of 200 pounds, a current score of 225 pounds, and a baseline, or starting weight, of 250 pounds. In order to generate a common scale between two or more different habits, such as health and conversation, a normalizedGoal and a normalizedBaseline can be generated. In the weight coaching example, the normalizedGoal can be 100 and the normalizedBaseline can be 50, to permit tracking negative progress. A normalized score of 0 can be used to represent moving in the opposite direction from the baseline by the amount of the goal. The following formula can be used to perform the conversion:

normalizedScore=normalizedGoal−
(normalizedBaseline*AbsoluteValue(goal−currentScore)/(goal−baseline))

Once a normalized score has been generated, a composite score can be computed by averaging two or more normalized scores. Further, a goal can be weighted to assign an increased or decreased amount of importance to that goal in generating a composite score. Additionally, a composite score can be computed for a habit by generating normalized scores for two or more sub-habits.

The overall habits summary 405 also can include individual habits summaries. For example, the overall habits summary 405 can include a separate conversation habits summary 420 that represents a user's progress at achieving one or more goals associated with the conversation habit. Further, the conversation habits summary 420 can include a conversation habits score 425 representing a user's current score for the one or more conversation habit goals being coached and a conversation habits baseline 430 representing the corresponding previous score. The overall score 410 and the conversation habits score 425 can be updated in near real-time based on the analysis performed by the coach server 230. For example, the overall score 410 and the conversation habits score 425 can be updated during a conversation based on how well the user is performing.

The overall habits interface 400 also can include a conversation habits tab 435. When a user selects the conversation habits tab 435, information describing the most recent conversation can be displayed. The most recent conversation interface 450 can include a conversation start time 455, a conversation end time 460, and a conversation location 465. In an implementation, the conversation start time 455 and the conversation end time 460 can be presented in a format that also includes date information.

Further, the most recent conversation interface 450 can include a metric selector 470. The metric selector 470 can be configured to present the user with a list of metrics that are available for viewing. For example, the metric selector 470 can comprise a drop-down menu. Using the metric selector 470, the user can select the conversation metric that is to be displayed, such as the percentage of time the user has spoken, the number of times the user has interrupted another participant, or a conversation summary for a predetermined period of time. The most recent conversation interface 450 also can include a metric legend 475 that explains elements of the graphical metric indicator 480, which depicts a metric associated with the most recent conversation. Additionally, the most recent conversation interface 450 can include a textual metric indicator 485 that presents one or more metrics in textual form. The graphical metric indicator 480 and the textual metric indicator 485 also can be updated in near real-time based on the analysis provided by the coach server 230.

In an implementation, the mobile personal services device 100 also can be configured to present non-visual feedback to the user, such as audio or haptic feedback, to convey information regarding the user's performance. For example, the personal device 110 can generate a signal that is audible only to the user to indicate that the user is talking too much. The personal device 110 also can be configured to vibrate in order to deliver feedback to the user.

Figure 5:
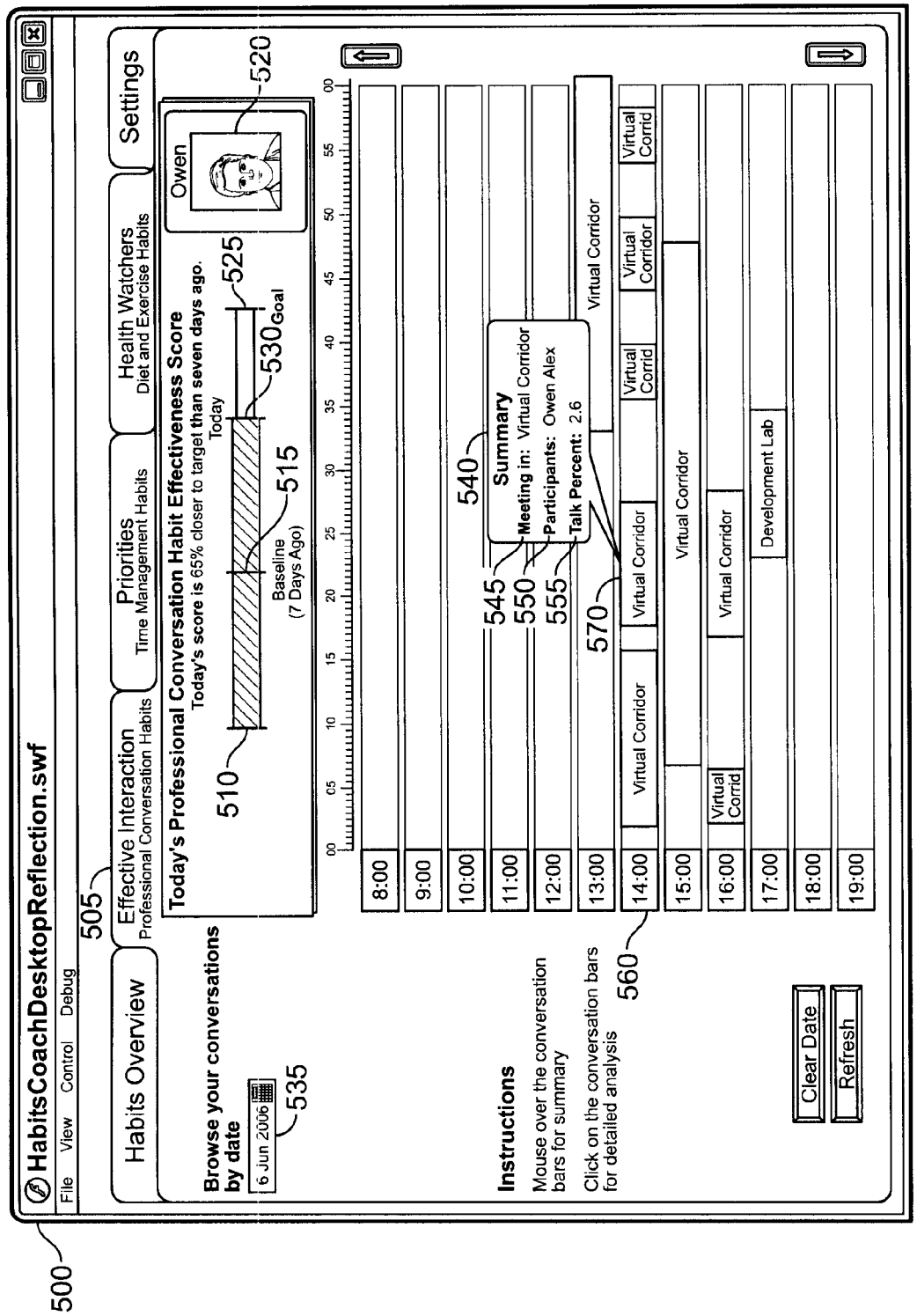
FIGS. 5 and 6 show conversation feedback provided through user interfaces.

FIG. 5 presents a habits coach client interface 500, which can be used to present time-delayed feedback on the coach client 220. The habits coach client interface 500 can be configured to include a conversation habits coach tab 505, which can include a daily effectiveness score 510. The daily effectiveness score 510 describes the progress a user has made in achieving the user's conversation goals. Further, the daily effectiveness score 510 can include a baseline 515, a goal 525, and a daily score 530. For example, if the metric is directed to the percentage of time spent listening by the user, the baseline 515 can represent previous performance in which the user listened for 25 percent of the conversation period, the daily score 530 can indicate that the user listened an average of 55 percent of the time during all of the user's conversations for that day, and the goal 525 can represent the target of listening 70 percent of the time.

The conversation habits coach tab 505 also can include a user's photo 520. Further, the conversations habits coach tab 505 can include a date selector 535 through which the user can select a particular date for which conversations can be reviewed. Additionally, the conversation habits coach tab 505 can include one or more timelines 560, each of which represents a particular unit of time, such as an hour. A timeline 560 also can include one or more conversation bars 570, which visually depict the start time, stop time, and duration associated with a conversation. Further, a conversation bar 570 can indicate the location at which the conversation took place. In an implementation, the timeline 560 also can include indicators associated with other habits, including gym visits and sleep patterns.

When a user selects a conversation bar 570, a conversation summary 540 associated with that conversation can be displayed. The conversation summary 540 can include a conversation location display 545, a conversation participants list 550, and a conversation metric readout 555. Additionally, selecting a conversation bar 570 permits a user to review the conversation associated with that bar. The conversation habits coach tab 505 also can be configured to display a summary of results for an entire day.

Figure 6:
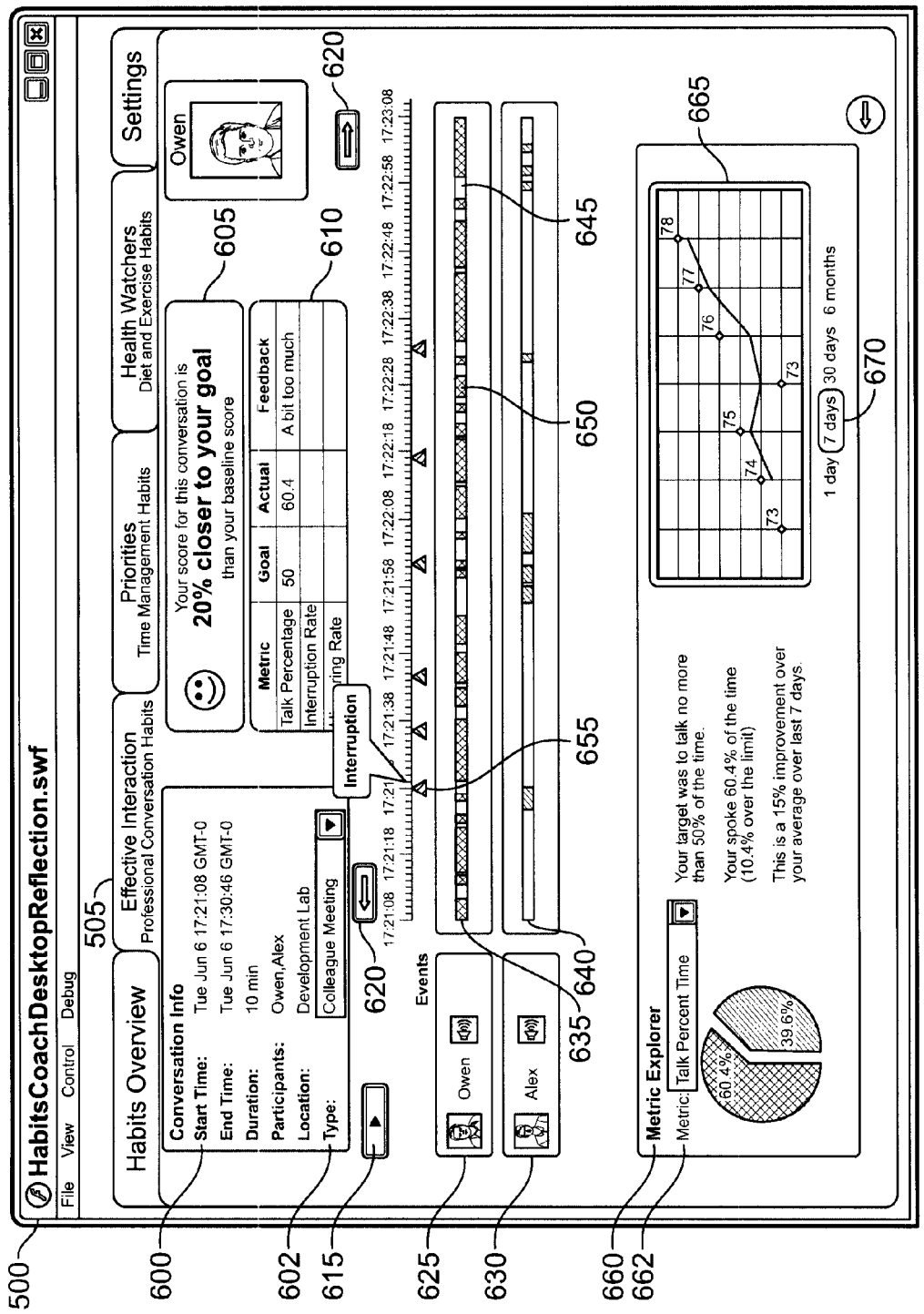

FIG. 6 depicts conversation specific time-delayed feedback provided on the coach client 220. As discussed above, the coach client 220 can include a habits coach client interface 500 featuring a habits coach tab 505. The coach client 220 can display conversation information 600 describing data associated with a particular conversation. For example, the conversation information 600 can include the conversation start time, conversation end time, conversation duration, conversation participants, the conversation location, and a conversation type selector 602. The user can categorize the type of conversation by selecting an option presented in the conversation type selector 602. The conversation can be categorized based on the object of the conversation or the participants, such as a presentation, sales call, team meeting, or a performance review. The conversation type specified through use of the conversation type selector 602 can be communicated to the coach server 230, which can reference the specified conversation type in performing analysis of the conversation.

The coach client 220 also can display a conversation score 605, which compares the user's actual performance with the user's goals for a specific conversation. Further, the coach client 220 can have a performance chart 610 that displays a list of metrics, a list of goals associated with those metrics, the results achieved by the user during the specific conversation, and feedback that can include one or more comments.

The coach client 220 also can include a playback control 615, which allows the user to replay the audio data comprising a specific conversation. Further, as only a small portion of a conversation may be viewable at a time, the coach client 220 can include scrolling buttons 620 that permit the user to scroll forward and backward within the conversation. Additionally, the coach client 220 can include a user label 625 that can include a picture of the user and the user's name, as well as one or more other participant labels 630 that identify other participants in the conversation.

The coach client 220 also can be configured to include a timeline 635 that graphically depicts the conversation with respect to a first participant. For example, one or more opaque blocks 650 can be used to indicate the points in time at which that participant was speaking and transparent blocks 645 can be used to indicate when that participant was quiet. Additionally, breaks at which there are no opaque blocks 650 or transparent blocks 645 can be used to identify points in time at which the participant left the conversation. Additional timelines, such as the timeline 640, can be used to depicts the behavior of additional participants. Different colors can be used to represent different participants. Because the timelines provide a temporal reconstruction of the conversation, one or more annotations 655 can be used to identify points at which particular events took place. For example, a collection of timelines 635 and 640 can include one or more annotations 655 to indicate when a first participant interrupted a second participant.

Additionally, the coach client 220 can include a metric explorer 660, which allows a user to graphically analyze one or more different conversation metrics. For example, the metric explorer 660 can include a time range selector 670 that allows the user to select a period of time for which the coach client 220 is to present a graphical analysis. The time range selector 670 can include a number of preset options, such as 1 day, 7 days, 30 days, and 6 months. The metric explorer 660 also can include a metric selector 662 that allows the user to specify the metric the metric explorer 660 will graphically analyze. For example, the metric selector 662 can be set to talk percent time, listen percent time, or interruptions per hour. Additionally, the metric explorer 660 can include a metric graph 665 that graphically presents analysis relating to a particular metric over a particular time period.

Figure 7:
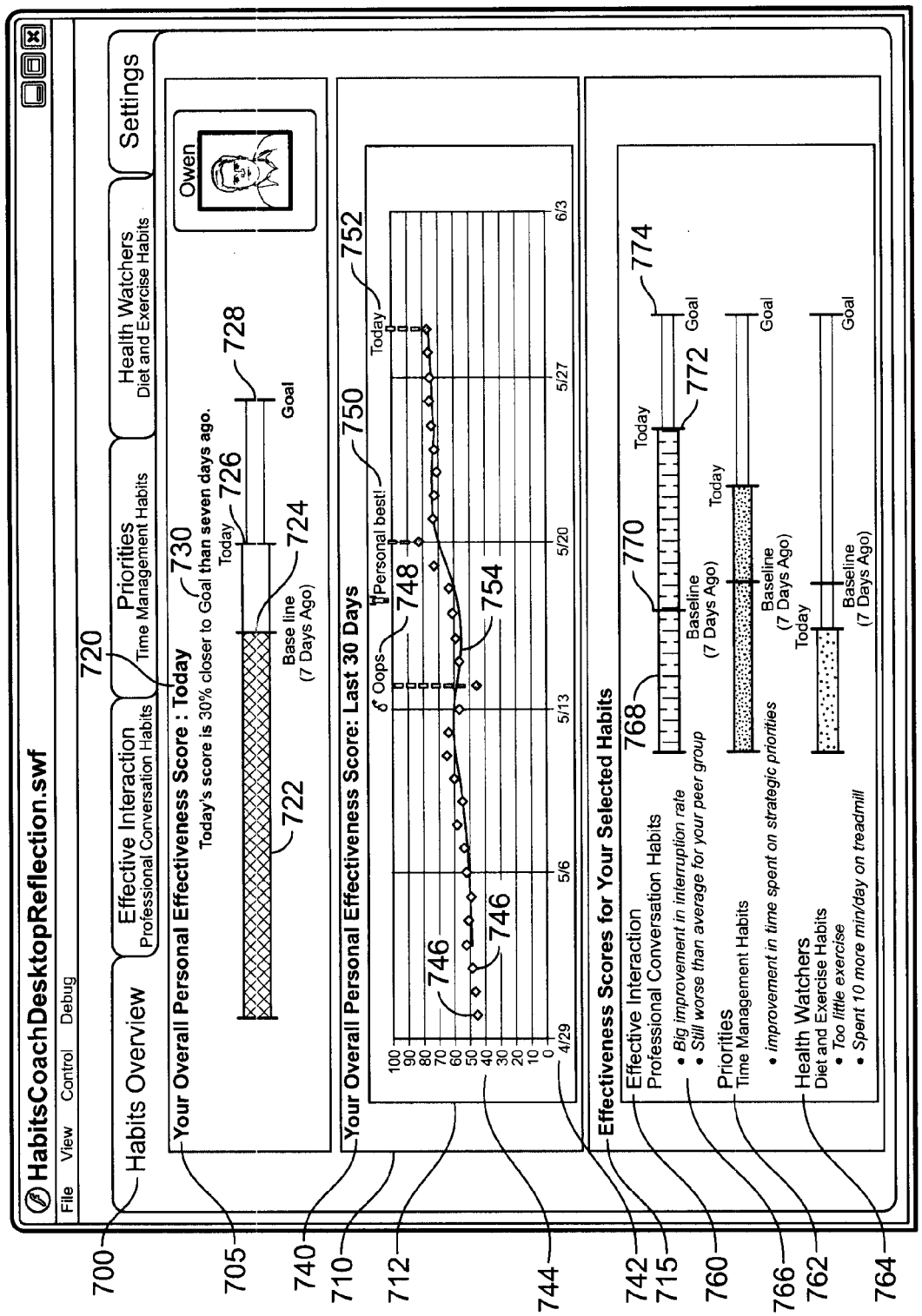
FIG. 7 shows a feedback summary provided through a user interface.

FIG. 7 presents a habits overview 700 that presents a user with a summary of scores relating to one or more habits. The habits overview 700 can be configured to include one or more separate summary boxes, such as a current effectiveness summary 705, an overall effectiveness summary 710, and an individual habits summary 715. The current effectiveness summary 705 can include a period identifier 720 that indicates the period with which the effectiveness score is associated, such as today. The current effectiveness summary 705 also can include a current effectiveness graph 722 that depicts one or more measures and goals associated with the current effectiveness score. For example, the current effectiveness graph 722 can present an effectiveness baseline 724 indicating a previous effectiveness score, such as a score from the previous week. The current effectiveness graph 722 also can be configured to present an effectiveness goal 728 that the user is trying to achieve. The user's current effectiveness score 726 can be graphically represented, such as by a bar, with respect to the effectiveness baseline 724 and the effectiveness goal 728. Additionally, the current effectiveness summary 705 can be configured to include an effectiveness statement 730 that expresses the user's effectiveness performance for the period.

The overall effectiveness summary 710 can be configured to present a graphical representation 712 of the user's effectiveness over a particular period, which is specified by the effectiveness period 740. The graphical representation 712 can include a horizontal axis 742 that identifies a plurality of units, such as individual dates, and a vertical axis 744 that also identifies a plurality of units, such as a scale of possible effectiveness scores. The user's effectiveness scores over the period can be indicated on the graphical representation 712 using a plurality of effectiveness score markers 746. Each effectiveness score marker 746 can indicate an effectiveness score associated with a particular date on the horizontal axis 742. One or more annotations also can be included on the graphical representation 712 to indicate significant events. For example, an effectiveness low marker 748 can identify the user's lowest effectiveness score for the period and an effectiveness high marker 750 can identify the user's personal best effectiveness score for the period. A current score marker 752 can be used to indicate the most recent effectiveness score. Additionally, a continuous marker 754 can be used to indicate an additional measure, such as a moving average for the period.

The individual habits summary 715 can be configured to present a score summary for one or more individual habits, such as a conversation habit 760, a priorities habit 762, and a diet and exercise habit 764. One or more feedback messages 766 can be associated with an individual habit to inform the user of her progress. An effectiveness graph also can be associated with an individual habit to graphically represent the user's progress in achieving a goal that corresponds to that habit. For example, a conversation effectiveness graph 768 can be associated with the conversation habit 760. As with the current effectiveness graph 722, the conversation effectiveness graph 768 can include a conversation effectiveness baseline 770 that indicates a previous score, a conversation effectiveness goal 774 that represents a target the user is trying to achieve, and a current conversation score 772 that represents the user's current effectiveness score for that habit.

In another implementation, the feedback information described above with reference to FIGS. 5-7 can be provided to the user on the mobile personal services device 100, such as through the personal device 110.

In still another implementation, the coaching system 200 also can be configured to host other applications using the personal mobile services device 100. A memory enhancement application can be executed to remind the user associated with the personal mobile services device 100 of information and events the user would like to recall. Additional details regarding the memory enhancement application are set forth in U.S. Pat. No. 7,035,091, the entirety of which is incorporated herein by reference. Further, the memory enhancement application can be configured to interact with one or more other components of the coaching system 200, such as location-based devices 210 and the personal mobile services devices 100 associated with other users.

The memory enhancement application can be configured to recognize another member of the coaching system 200 and to issue a reminder message to the user identifying that person. For example, the coach server 230 can determine the location of the user based on information supplied by a location-based device 210. When another member of the coaching system 200 comes into proximity with the user, such as entering the same room, the coach server can transmit a message to the user identifying the other member. The message can include any combination of an audio prompt played back through a speaker in the mobile personal services device 100, a text prompt output on a display of the mobile personal services device 100, and a graphical prompt, such as a photo, output on a display of the mobile personal services device 100. Individuals who are not part of the coaching system 200 also can be recognized, including through image analysis, voice print recognition, or electronic identification, such as recognition of a Bluetooth beacon.

The memory enhancement application also can be configured to remind the user of scheduled and unscheduled tasks. For example, a user can indicate that the mobile personal services device 100 is to remind the user to pick up laundry on the way home. A reminder then can be issued to the user based on a number of factors, including the time of day and data from one or more location-based sensors 210. For example, a location-based device 210 associated with an exit door can indicate to the coach server 230 that the user is leaving work. If the reminder includes a time component, such as after 4 p.m., the coach server 230 can determine whether that condition also is met. If all necessary conditions associated with the reminder are satisfied, a message can be transmitted from the coach server 230 to the user's mobile personal services device 100 to serve as a reminder.

A self-awareness application also can be hosted on the coaching system 200. The self-awareness application can be configured to utilize one or more sensors to track vital statistics relating to the user who is associated with the mobile personal services device 100. The statistics can be analyzed by the self-awareness application to monitor the user's wellness, including activity level, stress level, and physical health. For example, the mobile personal services device 100 can include a health monitor 130, such as a blood pressure or heart rate monitor. Data from the health monitor 130 can be analyzed by the self-awareness application running on the mobile personal services device 100 or the coach server 230, and feedback can be provided to the user. For example, a warning can be issued to the user if a dangerous increase or decrease in blood pressure is detected. Additionally, the user can review blood pressure readings that occurred over a particular period of time and can cross-correlate readings with temporally-related events.

A physical environment application also can be hosted on the coaching system 200 to assist a mobile personal services device 100 user in obtaining information relating to the surrounding environment. A user can enter a request to receive information relating to a particular subject through an interface on the mobile personal services device 100 or the coach client 220. Subsequently, when the user is within range of an information source, the information can be provided to the user through the mobile personal services device 100. For example, a user can enter a request to receive information relating to office supplies, including one or more specific items. A location-based device 210 or a beacon can be used to determine when the user is within range of an office supply source that includes one or more specified items. Further, a message, such as an audio or text message, can be provided to alert the user that the requested office supplies are available.

The physical environment application also can be used to provide information to the mobile personal services device 100 user in response to a real-time query. For example, the user can input a request to determine whether there is a restaurant within a particular range that will satisfy the user's dietary preferences. The coach server 230 can determine the user's location, such as through a location-based device 210 or a location sensor included in the mobile personal services device 100, and identify any matching restaurants within range. Further, the user can request additional information and services based on the information provided by the coach server 230, including directions, daily specials, menu options, and reservations.

A communication management application also can be hosted on the coaching system 200 to provide assistance with communication-based needs. The communication management application can be used to locate a particular person or entity with whom the user would like to communicate. For example, a mobile personal services device 100 user can instruct the communication management application to locate a co-worker. The communication management application can then attempt to contact the co-worker through a variety of different channels, including known telephone numbers, instant messaging, and electronic mail. The communication management application also can examine reporting messages sent to the coach server 230 by the location-based devices 210 to identify the co-worker's present location. Once the co-worker has been contacted or located, the mobile personal services device 100 user can be signaled to begin the communication session.

Additionally, the communication management application can be configured to locate a point of contact to address a particular problem. The mobile personal services device 100 user can provide an abstract description of the problem or the person with whom the user would like to communicate. Based on the abstract description, the communication management application can identify an appropriate point of contact and notify the user, such as through a text message or by establishing a communication session. Additionally, one or more items of data associated with the user can be referenced to assist in the identification of the appropriate point of contact.

For example, the user can specify that she would like to have her car serviced. In response to this request, the communication management application can access the user's information to identify the type of car. Further, the communication management application can identify appropriate service locations based on an address associated with the user. The communication management application can then display one or more of the appropriate service locations to the user. Additionally, the communication management application also can be configured to establish contact with the most appropriate service provider and signal the user.

Figure 8:
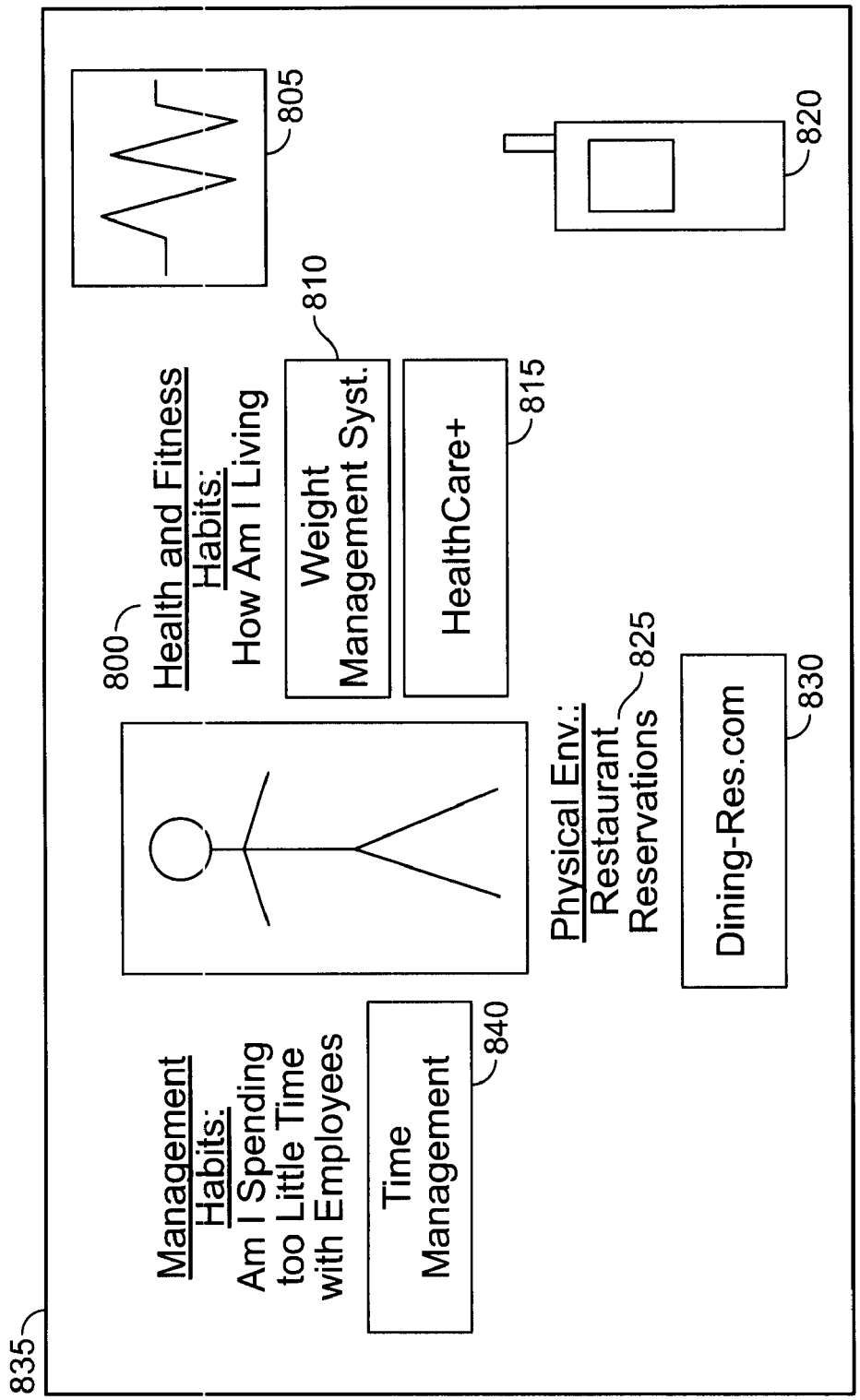
FIG. 8 shows associating content and logos of sponsors with hosted applications.

FIG. 8 depicts applications hosted on the coaching system 200 for use with a mobile personal services device 100, which can be sponsored by a third-party. As discussed above, an application can be used to provide coaching to a user regarding one or more habits, including health and fitness habits 800. Also as discussed above, an application can be generated in accordance with standardized sensor data formats and rules. The mobile personal services device 100 associated with the user can include one or more health and fitness data sensors 805 for monitoring the user's biometric information, such as activity, vital signs, and nutrition. Additionally, the health and fitness habit application can be sponsored by a third party in the health and fitness industry, such as a weight management system, fitness club, or healthcare provider. A logo also can be presented with the health and fitness habit application to identify the sponsorship, such as the weight management system logo 810 and/or the healthcare provider logo 815. A logo associated with a third-party sponsor further can be associated with particular items of information provided to the user within the health and fitness habit, such as sponsored content provided for use within the habit.

A personal mobile services device 100 also can be configured to include a location sensor 820, such as a GPS receiver, which can support one or more applications, including a physical environment application 825. Thus, the personal mobile services device 100 user can request a service through the physical environment application 825 based on the user's current location. For example, the user can request information about restaurants within a specific range, such as one block or one mile. Further, the user can specify the request such that it will filter results in accordance with one or more specified criteria. Additionally, one or more portions of the physical environment application 825 also can be sponsored by a third party. For example, a restaurant reservations module can be sponsored by a reservation service and can be branded with the reservation service logo 830.

Third party sponsorship of content and services, and branding associated with such third party sponsors also can be expanded to other applications hosted in the coaching system 200. For example, a management habits application 835 can be associated with a time management advisor or efficiency expert. The sponsor can provide content, including time management tools, for use within the management habits application 835. Additionally, the sponsor provided content can be displayed in conjunction with the sponsor's logo, such as a time management advisor logo 840. Thus, one or more applications hosted in the coaching system 200 can be associated with content provided by one or more sponsors and one or more logos identifying those sponsors.

Figure 9A:
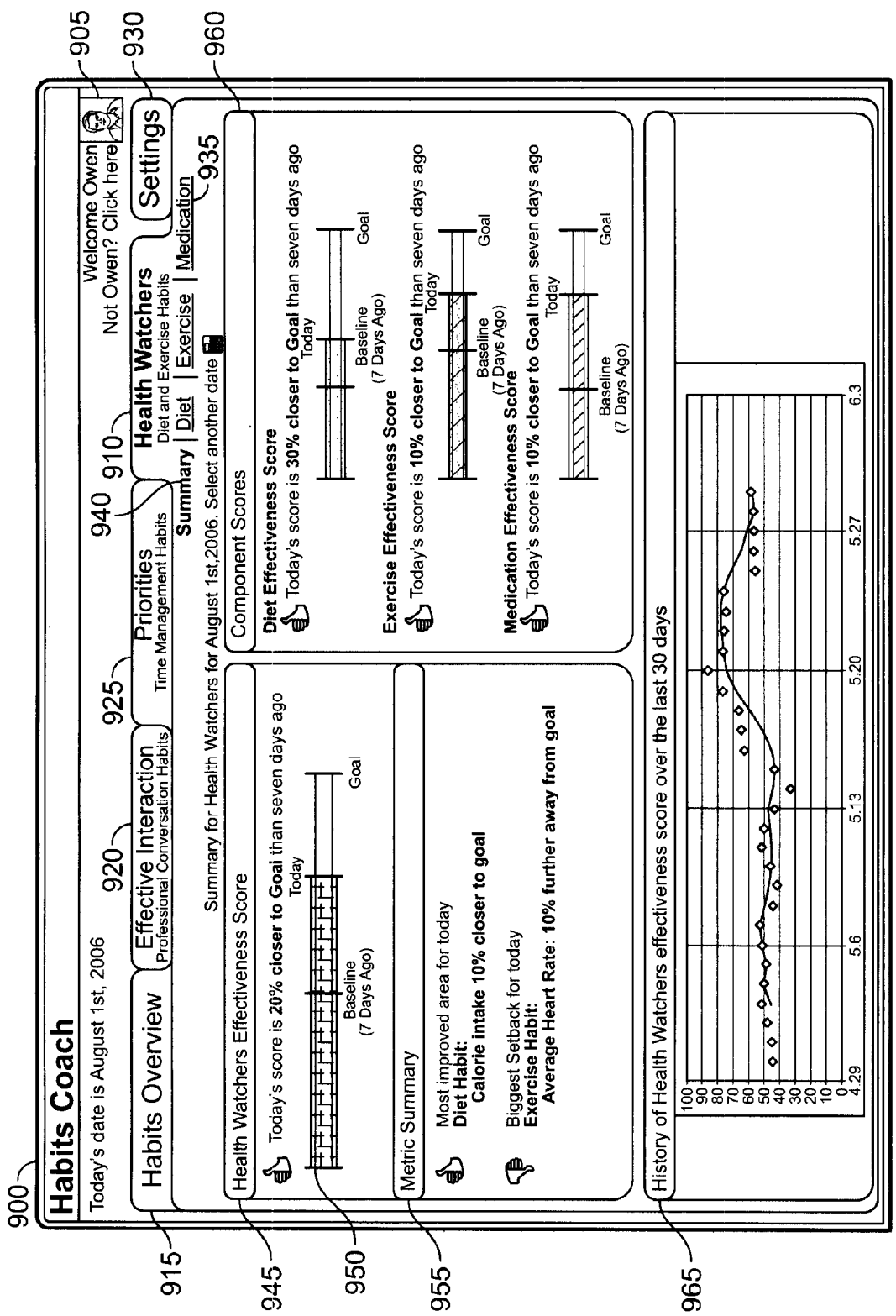

FIGS. 9A-9E show a habits coach interface 900, such as a coaching interface that can be provided to a user through a mobile personal services device 100 or a coach client 220. FIG. 9A shows the habits coach interface associated with a particular user, who is identified by a name and/or picture 905. The habits coach interface 900 can be configured to include one or more tabs, which correspond to a habit or topic. The HealthWatchers tab 910 is presently selected and displayed in the habits coach interface 900. The habits coach interface 900 also includes a habits overview tab 915, an Effective Interaction tab 920, a Priorities tab 925, and a settings tab 930. The HealthWatchers tab 910 further can include one or more views 935, which can be selected to present particular information within the HealthWatchers tab 910. For example, a summary view 940 can be selected to present a summary of the HealthWatchers tab 910.

The summary view 940 of the HealthWatchers tab 910 can include an overall effectiveness score 945 that indicates progress toward an overall goal. The overall effectiveness score 945 can be a composite of two or more individual goals, which can be assigned individual weights. The overall effectiveness score 945 can be described in terms of a percentage change over a particular period of time. Further, the overall effectiveness score 945 can be graphically depicted using an overall effectiveness progress bar 950.

The summary view 940 of the HealthWatchers tab 910 also can include a metric summary 955, depicting scores in one or more areas. For example, the metric summary 955 can indicate the most improved metric for a predetermined period of time, such as one day or one week. The metric summary 955 also can indicate the area with the least improvement or greatest set back for the predetermined period of time. Further, the summary view 940 can include a plurality of component scores 960, depicting progress with respect to individual measurement areas. For example, the component scores 960 can include scores representing diet effectiveness, exercise effectiveness, and medication effectiveness. The component scores 960 can be combined to generate the overall effectiveness score 945. Additionally, the summary view 940 can include a history chart 965 depicting the overall effectiveness score 945 over a predetermined period of time, such as 30 days.

Figure 9B:
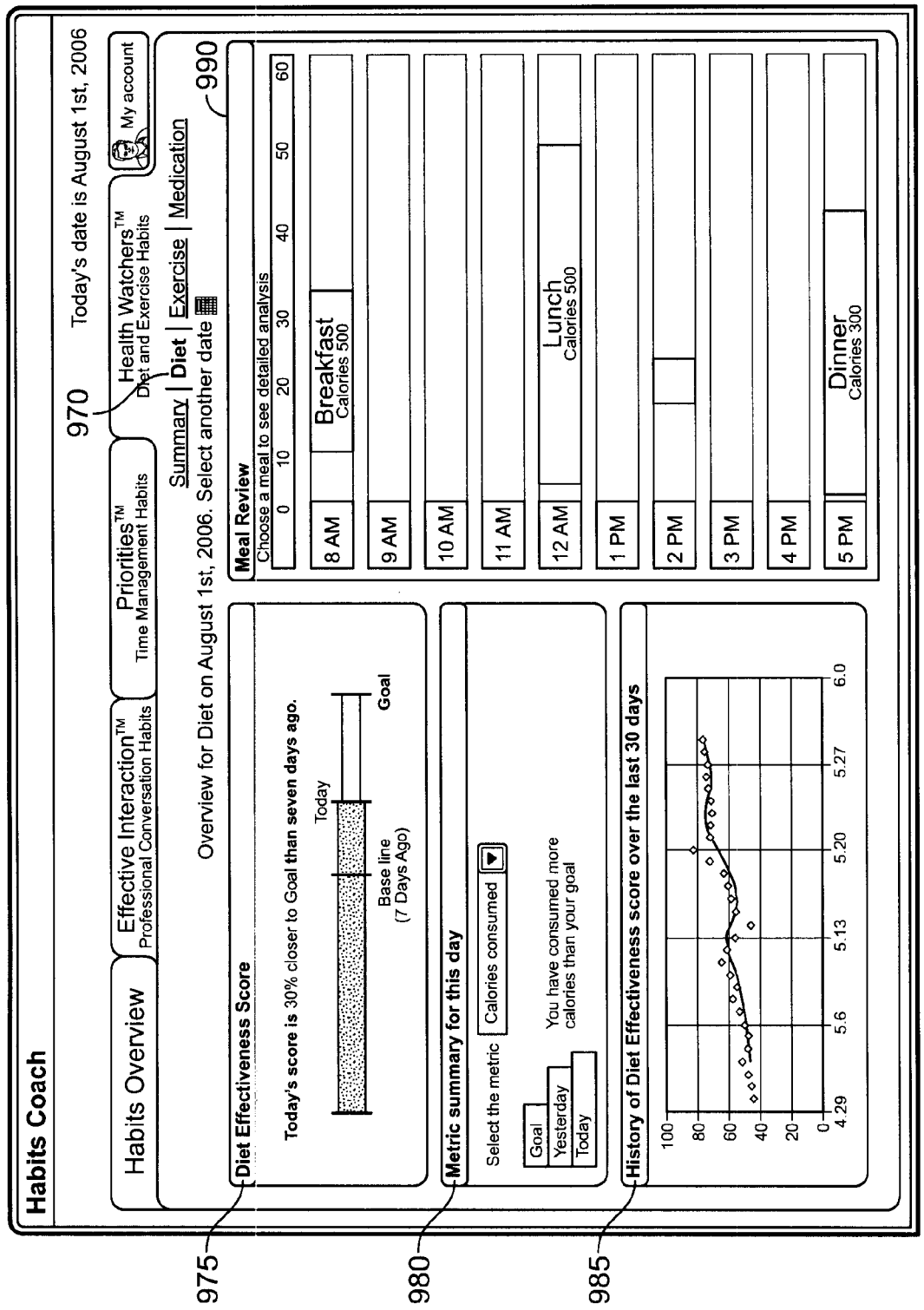
Figure 9C:
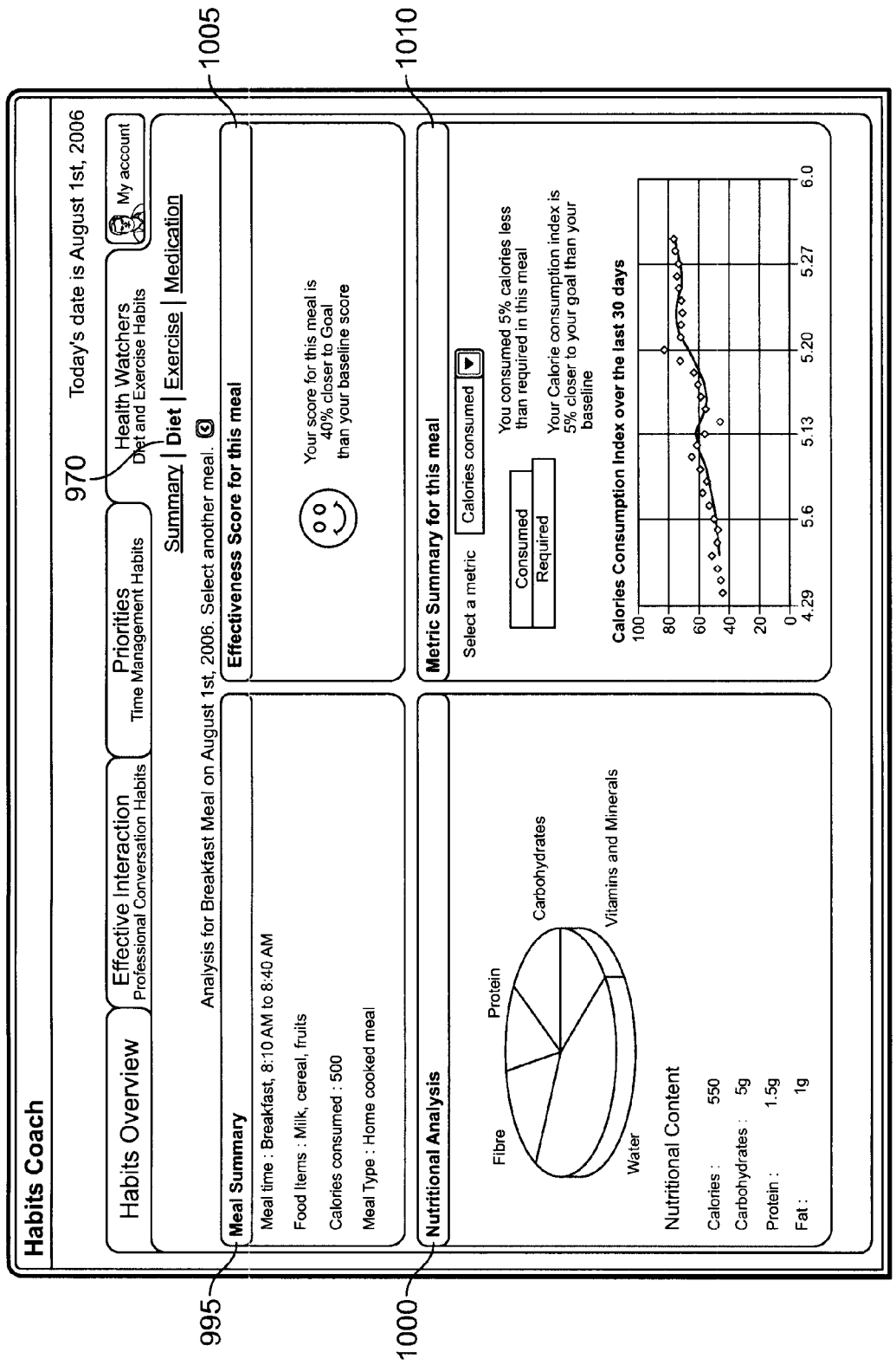

FIGS. 9B and 9C show the diet view 970 of the HealthWatchers tab 910. The diet view 970 can be configured to present information relating to the eating habits of the user, including the time, amount, and nutritional value of foods that are eaten. The diet view 970 can include a diet effectiveness score 975, corresponding to the diet effectiveness score of the component scores 960, which can be described in terms of a percentage change over a particular period of time. Further, the diet effectiveness score 975 can be graphically depicted using a progress bar. The diet view 970 also can include a metric summary 980 depicting one or more individual metrics corresponding to diet. For example, the metric summary 980 can include a metric relating to caloric consumption for a predetermined time period, such as a day or a meal. In an implementation, the metric summary also can include nutritional information, such as the percentage of the recommended daily allowance of one or more vitamins that have been consumed or the percentage of fat consumed. Additionally, the diet view 970 can present history chart 985 depicting the diet effectiveness score 975 over a predetermined period of time, such as 30 days. The diet view 970 further can include a meal review 990, showing the times at which meals were taken and the calories consumed at each meal for a predetermined time period, such as the present day.

In an implementation, additional details corresponding to a meal can be accessed by selecting the meal. If a meal is selected, a meal summary 995 can be presented. The meal summary 995 can include information such as the time and date on which the meal was consumed, the food items included in the meal, and the calories consumed. The meal summary 995 also can indicate the type of meal, such as home cooked, restaurant, or fast food. A nutritional analysis 1000 also can be presented to provide further information about the selected meal. The nutritional analysis 1000 can present the nutritional content, including the calories, carbohydrates, proteins, fats, fiber, water, and vitamins and minerals included in the meal. The nutritional analysis 1000 can be presented graphically, textually, or as a combination thereof.

A meal effectiveness score 1005 also can be presented, indicating the contribution of the meal toward a goal, such as the overall diet goal or a nutritional goal. Selecting a meal also can cause a metric summary 1010 for the meal to be displayed. The metric summary 1010 can be presented in terms of one or more metrics, which the user can select from a menu of one or more available metrics. The metric summary 1010 can indicate a measure for the meal associated with the selected one or more metrics. Further, the metric summary 1010 also can indicate a historical measure for the selected one or more metrics, such as in a graph or chart.

Figure 9D:
Figure 9E:
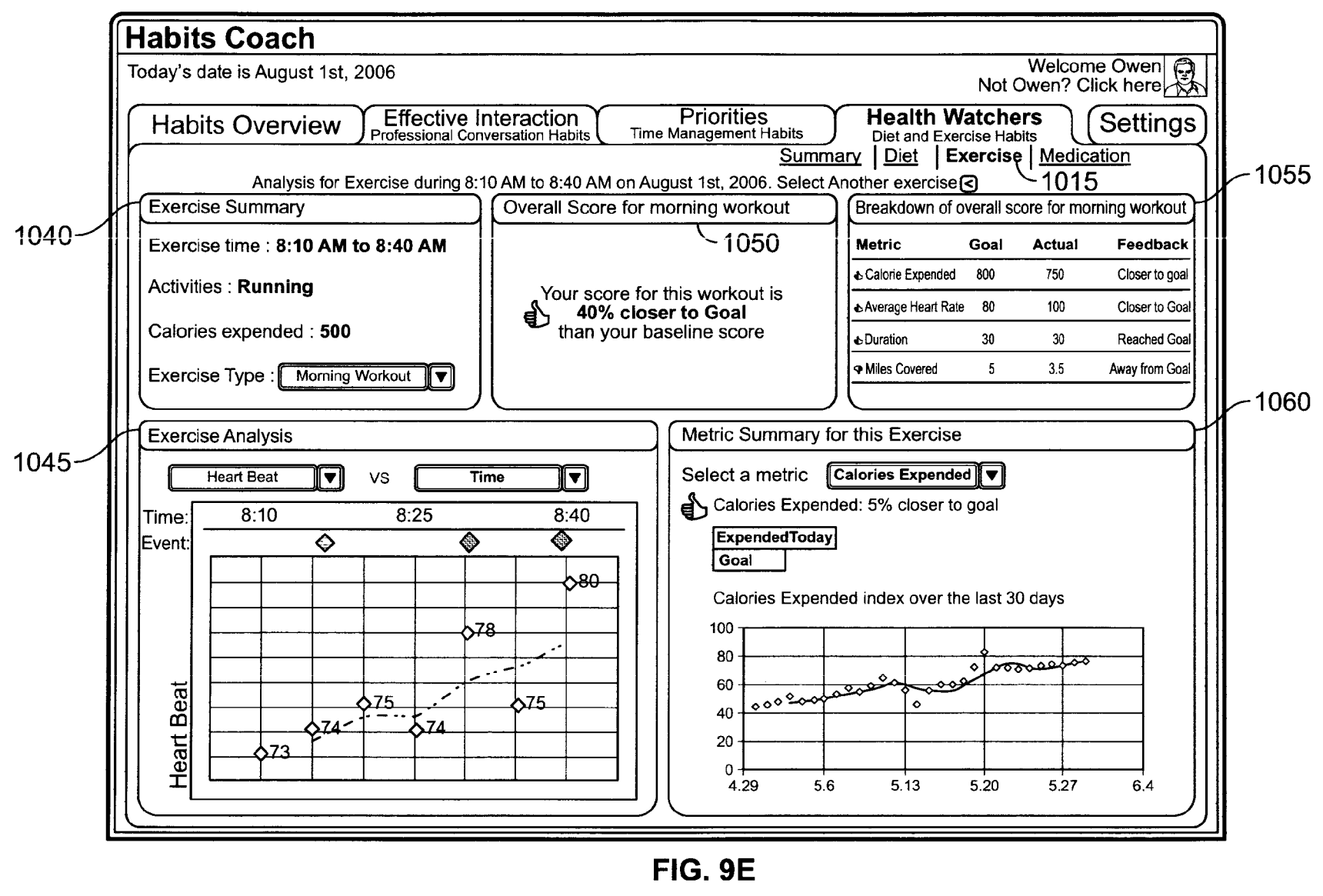

FIGS. 9D and 9E show the exercise view 1015 of the HealthWatchers tab 910. The exercise view 1015 can be configured to present information relating to the exercise or fitness habits of the user, including the time, amount, and type of exercise that was performed. The exercise view 1015 can include an exercise effectiveness score 1020, corresponding to the exercise effectiveness score of the component scores 960, which can be described in terms of a percentage change over a particular period of time. Further, the exercise effectiveness score 1020 can be graphically depicted using a progress bar. The exercise view 1015 also can include a metric summary 1025 for a particular period of time, such as the present day. The metric summary 1025 can include a list of one or more selectable metrics, such as calories expended. The metric summary 1025 can present the selected metric in relationship to a predetermined goal.

The exercise view 1015 also can include a history of the exercise effectiveness score 1030, which can graphically depict the progress of the exercise effectiveness score over a predetermined time period, such as 30 days. Further, the exercise view 1015 can include a workout review 1035, which can indicate the type of exercise performed, the time at which the exercise was performed, and the amount of calories expended.

In an implementation, additional details corresponding to a workout can be accessed by selecting the workout. If a workout is selected, an exercise summary 1040 can be presented. The exercise summary 1040 can include information such as the time of the workout, the activity performed, the calories expended, and the type of exercise, such as a morning or evening workout. Further, an exercise analysis 1045 can be presented, including in a graphical form. The exercise analysis 1045 can be used to compare two or more metrics for a workout. For example, a user can select heart beat and time to generate an exercise analysis 1045 depicting heart beat over time for at least a portion of the workout. In an implementation, the HealthWatchers tab 910 can be configured to use one or more default values, which can be changed by a user.

An overall score 1050 also can be presented for the selected workout, indicating progress toward an overall goal based on the selected workout. Further, a breakdown of scores 1055 can be presented, indicating performance with respect to a goal for one or more metrics. For example, the breakdown of scores 1055 can include a metric associated with calories expended. The breakdown of scores 1055 also can indicate the actual calories expended in comparison to the calorie goal. Further, the breakdown of scores 1055 can include feedback reflective of the comparison. Additionally, the breakdown of scores 1055 can include scores specific to a particular form of exercise. For example, if the form of exercise is running, the breakdown of scores 1055 can include a score relating to miles covered or speed.

An exercise metric summary 1060 also can be presented for a particular workout. The exercise metric summary 1060 can depict performance with respect to a particular metric, such as a default metric or a user selected metric. Further, the exercise metric summary 1060 can depict progress toward a goal associated with the metric for a particular day and/or progress over a predetermined period of time, such as 30 days. The progress corresponding to the metric can be displayed textually, graphically, or in a combination thereof.

Figure 10:
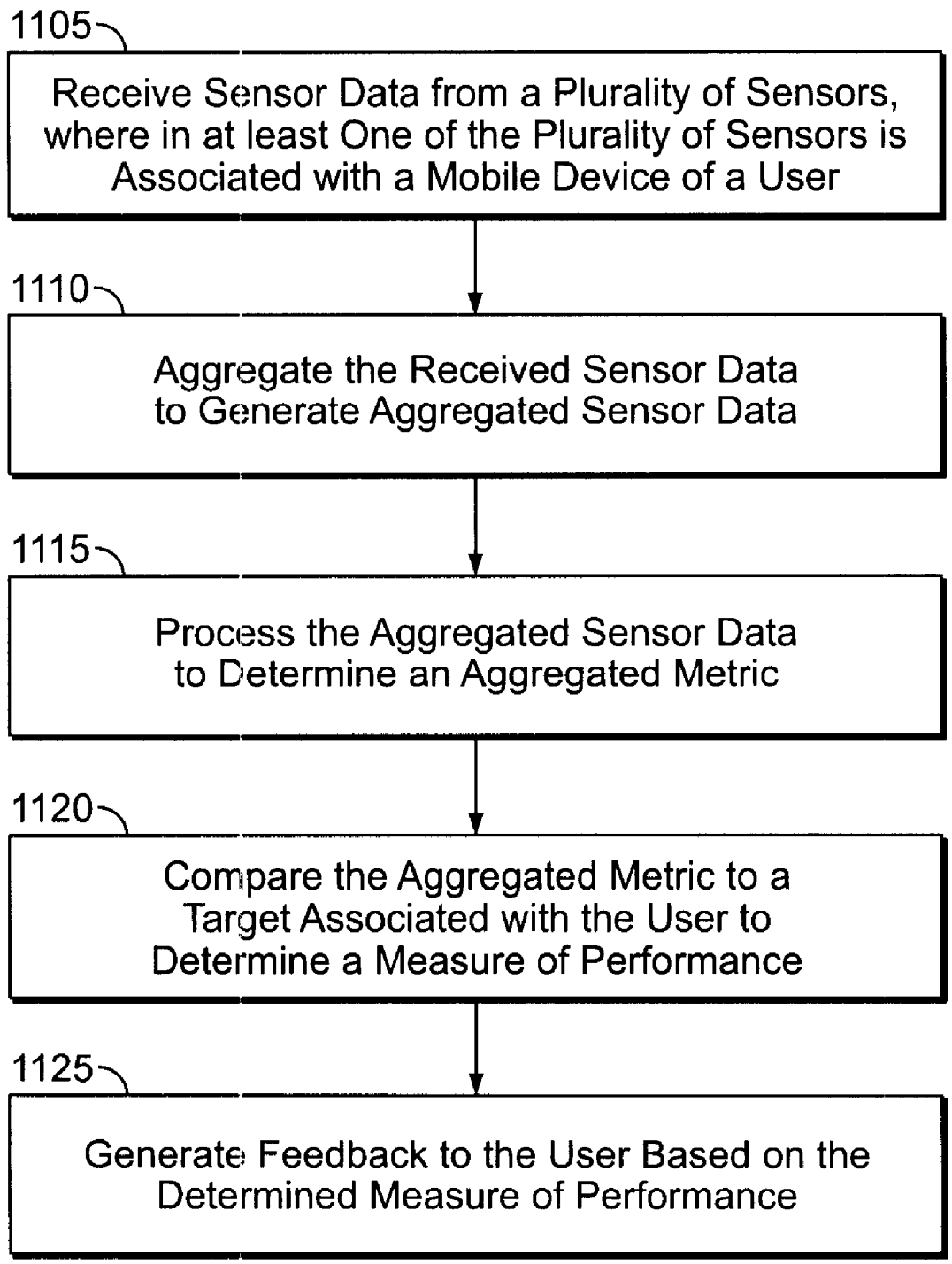
FIG. 10 shows a flowchart for providing feedback.
Like reference symbols indicate like elements throughout the specification and drawings.

FIG. 10 shows a flowchart for generating feedback. Initially, sensor data is received from a plurality of sensors, wherein at least one of the plurality of sensors is associated with a mobile device of a user (1105). The received sensor data is aggregated to generate aggregated sensor data (1110). The aggregated sensor data is processed to determine an aggregated metric (1115). The aggregated metric is compared to a target associated with the user to determine a measure of performance (1120). Once the measure of performance has been determined, feedback based on the determined measure of performance is generated to the user (1125).

A number of implementations have been disclosed herein. Nevertheless, it will be understood that various modifications may be made without departing from the spirit and scope of the claims. Accordingly, other implementations are within the scope of the following claims.

What is claimed is:

1. A method of providing feedback, the method comprising:
   receiving sensor data from a plurality of sensors, wherein at least one of the plurality of sensors is an audio sensor associated with a mobile device of a user;
   aggregating the received sensor data to generate aggregated sensor data;
   analyzing the content of a conversation between the user and another person, using at least a portion of the aggregated sensor data;
   in response to analyzing the content of the conversation, determining an aggregated metric relating to an effectiveness of the user in communicating with the other person during the conversation;
   comparing the aggregated metric to a user-defined conversation habit target to determine a conversation score; and
   providing a conversation interface to the user, the conversation interface including feedback regarding the effectiveness of the user in communicating with the other person during the conversation, the feedback including the aggregated metric, the user-defined conversation habit target, and the conversation score,
   wherein:
      determining the aggregated metric further comprises determining, based on one or more of the words, that the user has made a specific point during the conversation, and
      comparing the aggregated metric further comprises comparing the specific point to a user-defined checklist of points that the user intends to make during the conversation, and
      providing the conversation interface further comprises providing information to the user that identifies one or more points that the user has not yet made during the conversation.

2. The method of claim 1, wherein the mobile device comprises a mobile personal services device that includes two or more of an audio sensor, a video sensor, an environmental sensor, a biometric sensor, a location sensor, an activity detector, and a health monitor.

3. The method of claim 2, further comprising displaying the conversation interface on the mobile device.

4. The method of claim 3, further comprising displaying the feedback in near real-time to receiving the sensor data.

5. The method of claim 1, wherein the sensor data is received in real-time.

6. The method of claim 2, further comprising:
   receiving location data from a location-based device indicating a current position of the mobile device; and
   processing the aggregated sensor data in accordance with the received location data.

7. The method of claim 2, wherein at least one of the plurality of sensors is associated with a mobile device of another user.

8. The method of claim 1, further comprising:
   processing the received sensor data associated with at least one of the plurality of sensors to determine a second metric; and
   computing a composite score based on the aggregated metric and the second metric,
   wherein the feedback further includes the composite score.

9. The method of claim 1, further comprising:
   identifying the other person, using at least a portion of the aggregated sensor data, responsive to identifying the other person, selecting the user-defined conversation habit target associated with the other person, from among multiple user-defined conversation habit targets.

10. The method of claim 9, wherein the conversation habit target specifies a number of times that the user defines as acceptable to interrupt the other person during the conversation.

11. The method of claim 1, wherein determining the aggregated metric further comprises:
determining an amount of time that the user spent talking during the conversation, and
determining an amount of time that the user spent listening during the conversation.

12. The method of claim 1, wherein determining the aggregated metric further comprises:
determining, based on one or more of the words, a number of questions asked by the user.

13. The method of claim 1, further comprising:
determining that the conversation has begun when the aggregated sensor data indicates that the user has entered a room in which the other person is present.

14. The method of claim 1, further comprising:
determining that the conversation has begun when the aggregated sensor data indicates that the user is within a predetermined distance of the other person, and that at least one of the user or the other person are speaking.

15. The method of claim 1, further comprising:
determining that the conversation has begun when the aggregated sensor data indicates that the user and the other person have spoken for more than a predetermined amount of time.

16. The method of claim 1, wherein the feedback further comprises information identifying a start time of the conversation, an end time of the conversation, and a location of the conversation.

17. A system for providing feedback, the system comprising:
one or more computers; and
a non-transitory computer-readable medium coupled to the one or more computers having instructions stored thereon which, when executed by the one or more computers, cause the one or more computers to perform operations comprising:
receiving sensor data from a plurality of sensors, wherein at least one of the plurality of sensors is an audio sensor associated with a mobile device of a user;
aggregating the received sensor data to generate aggregated sensor data;
analyzing the content of a conversation between the user and another person, using at least a portion of the aggregated sensor data;
in response to analyzing the content of the conversation, determining an aggregated metric relating to an effectiveness of the user in communicating with the other person during the conversation;
comparing the aggregated metric to a user-defined conversation habit target to determine a conversation score; and
providing a conversation interface to the user, the conversation interface including feedback regarding the effectiveness of the user in communicating with the other person during the conversation, the feedback including the aggregated metric, the user-defined conversation habit target, and the conversation score,
wherein:
determining the aggregated metric further comprises determining, based on one or more of the words, that the user has made a specific point during the conversation, and
comparing the aggregated metric further comprises comparing the specific point to a user-defined checklist of points that the user intends to make during the conversation, and
providing the conversation interface further comprises providing information to the user that identifies one or more points that the user has not yet made during the conversation.

18. A non-transitory computer readable medium encoded with a computer program for providing feedback, the program comprising instructions that when executed by data processing apparatus cause the data processing apparatus to perform operations comprising:
receiving sensor data from a plurality of sensors, wherein at least one of the plurality of sensors is an audio sensor associated with a mobile device of a user;
aggregating the received sensor data to generate aggregated sensor data;
analyzing the content of a conversation between the user and another person, using at least a portion of the aggregated sensor data;
in response to analyzing the content of the conversation, determining an aggregated metric relating to an effectiveness of the user in communicating with the other person during the conversation;
comparing the aggregated metric to a user-defined conversation habit target to determine a conversation score; and
providing a conversation interface to the user, the conversation interface including feedback regarding the effectiveness of the user in communicating with the other person during the conversation, the feedback including the aggregated metric, the user-defined conversation habit target, and the conversation score,
wherein:
determining the aggregated metric further comprises determining, based on one or more of the words, that the user has made a specific point during the conversation, and
comparing the aggregated metric further comprises comparing the specific point to a user-defined checklist of points that the user intends to make during the conversation, and
providing the conversation interface further comprises providing information to the user that identifies one or more points that the user has not yet made during the conversation.

* * * * *